United States Patent
Grau et al.

(10) Patent No.: US 8,579,849 B2
(45) Date of Patent: *Nov. 12, 2013

(54) PYLORIC VALVE DEVICES AND METHODS

(75) Inventors: Buket Grau, Arlington, MA (US);
David Robert Gale, Cambridge (GB);
Sam Anne Musgrave, Cambridge (GB);
George McGee Perkins, Cambridge (GB); Mark Jeffrey Edhouse, Levin (NZ); Marc Graham, Somerville, MA (US); Christopher Kadamus, Jamaica Plain, MA (US)

(73) Assignee: E2 LLC, Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/363,509

(22) Filed: Feb. 1, 2012

(65) Prior Publication Data
US 2012/0136457 A1 May 31, 2012

Related U.S. Application Data

(63) Continuation of application No. 12/384,890, filed on Apr. 9, 2009, now Pat. No. 8,142,385.

(60) Provisional application No. 61/206,048, filed on Jan. 27, 2009, provisional application No. 61/123,472, filed on Apr. 9, 2008.

(51) Int. Cl.
*A61M 5/00* (2006.01)
*A61F 2/04* (2013.01)

(52) U.S. Cl.
USPC .............. 604/9; 604/8; 623/23.65; 623/23.68

(58) Field of Classification Search
USPC .............. 604/8, 9, 544, 909; 623/23.65–23.7, 623/1.5, 1.36, 1.11–1.13
See application file for complete search history.

(56) References Cited

U.S. PATENT DOCUMENTS

| | | | |
|---|---|---|---|
| 4,315,509 | A | 2/1982 | Smit |
| 4,501,264 | A | 2/1985 | Rockey |
| 5,306,300 | A | 4/1994 | Berry |
| 5,401,241 | A | 3/1995 | Delany |
| 5,820,584 | A | 10/1998 | Crabb |
| 5,993,473 | A | 11/1999 | Chan et al. |

(Continued)

FOREIGN PATENT DOCUMENTS

| | | |
|---|---|---|
| WO | WO 03/086247 | 10/2003 |
| WO | WO 2006/127593 | 11/2006 |
| WO | WO 2007/030829 | 3/2007 |
| WO | WO 2007/053556 | 5/2007 |

*Primary Examiner* — Philip R Wiest
(74) *Attorney, Agent, or Firm* — Joseph P. Errico

(57) ABSTRACT

A pyloric valve is provided for inhibiting the flow of chyme through the pyloric region of the gastrointestinal tract. The pyloric valve includes a blocking portion having a disc-shaped inlet and a helical flange. The helical flange may be disposed in a contracted position defining a contracted length and a contracted diameter and an extended position defining an extended length and an extended diameter, wherein the extended length is longer than the contracted length and the extended diameter is smaller than the contracted diameter. The pyloric valve may further include a sleeve that may have a beveled distal end. The pyloric valve may be constructed of silicon. Also provided are methods of inserting and removing the pyloric valve, which each include a step of manipulating the support between its contracted and extended positions. Insertion and removal systems are also provided for use with the pyloric valve.

13 Claims, 37 Drawing Sheets

(56) References Cited

U.S. PATENT DOCUMENTS

| | | |
|---|---|---|
| 6,271,278 B1 | 8/2001 | Park et al. |
| 6,454,785 B2 | 9/2002 | De Hoyos Garza |
| 6,540,789 B1 | 4/2003 | Silverman et al. |
| 6,544,291 B2 | 4/2003 | Taylor |
| 6,558,400 B2 | 5/2003 | Deem et al. |
| 6,675,809 B2 | 1/2004 | Stack et al. |
| 6,740,121 B2 | 5/2004 | Geitz |
| 6,755,869 B2 | 6/2004 | Geitz |
| 6,764,518 B2 | 7/2004 | Godin |
| 6,802,868 B2 | 10/2004 | Silverman et al. |
| 6,845,776 B2 | 1/2005 | Stack et al. |
| 6,946,002 B2 | 9/2005 | Geitz |
| 6,981,978 B2 | 1/2006 | Gannoe |
| 6,994,095 B2 | 2/2006 | Burnett |
| 7,025,791 B2 | 4/2006 | Levine et al. |
| 7,033,384 B2 | 4/2006 | Gannie et al. |
| 7,037,343 B2 | 5/2006 | Imran |
| 7,037,344 B2 | 5/2006 | Kagan et al. |
| 7,044,979 B2 | 5/2006 | Silverman et al. |
| 7,090,699 B2 | 8/2006 | Geitz |
| 7,097,665 B2 | 8/2006 | Stack et al. |
| 7,111,627 B2 | 9/2006 | Stack et al. |
| 7,118,600 B2 | 10/2006 | Dua et al. |
| 7,121,283 B2 | 10/2006 | Stack et al. |
| 7,122,058 B2 | 10/2006 | Levine et al. |
| 7,152,607 B2 | 12/2006 | Stack et al. |
| 7,214,233 B2 | 5/2007 | Gannoe et al. |
| 7,220,284 B2 | 5/2007 | Kagan et al. |
| 7,267,694 B2 | 9/2007 | Levine et al. |
| 8,142,385 B2 * | 3/2012 | Grau et al. ........................ 604/8 |
| 2003/0040808 A1 | 2/2003 | Stack et al. |
| 2003/0199989 A1 | 10/2003 | Stack et al. |
| 2003/0199990 A1 | 10/2003 | Stack et al. |
| 2003/0199991 A1 | 10/2003 | Stack et al. |
| 2004/0117031 A1 | 6/2004 | Stack et al. |
| 2004/0122526 A1 | 6/2004 | Imran |
| 2004/0148034 A1 | 7/2004 | Kagan et al. |
| 2004/0172141 A1 | 9/2004 | Stack et al. |
| 2004/0172142 A1 | 9/2004 | Stack et al. |
| 2004/0204768 A1 | 10/2004 | Geitz |
| 2004/0220682 A1 | 11/2004 | Levine et al. |
| 2004/0267378 A1 | 12/2004 | Gazi et al. |
| 2005/0004430 A1 | 1/2005 | Lee et al. |
| 2005/0004681 A1 | 1/2005 | Stack et al. |
| 2005/0080491 A1 | 4/2005 | Levine et al. |
| 2005/0085923 A1 | 4/2005 | Levine et al. |
| 2005/0096750 A1 | 5/2005 | Kagan et al. |
| 2005/0125020 A1 | 6/2005 | Meade et al. |
| 2005/0177181 A1 | 8/2005 | Kagan et al. |
| 2005/0192614 A1 | 9/2005 | Binmoeller |
| 2005/0273060 A1 | 12/2005 | Levy et al. |
| 2006/0009858 A1 | 1/2006 | Levine et al. |
| 2006/0064120 A1 | 3/2006 | Levine et al. |
| 2006/0129237 A1 | 6/2006 | Imran |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0265082 A1 | 11/2006 | Meade et al. |
| 2006/0287734 A1 | 12/2006 | Stack et al. |
| 2007/0005147 A1 | 1/2007 | Levine et al. |
| 2007/0010865 A1 | 1/2007 | Dann et al. |
| 2007/0032879 A1 | 2/2007 | Levine et al. |
| 2007/0083224 A1 | 4/2007 | Hively |
| 2007/0135831 A1 | 6/2007 | Burnett |
| 2007/0149994 A1 | 6/2007 | Sosnowski et al. |
| 2007/0156248 A1 | 7/2007 | Marco et al. |
| 2007/0178160 A1 | 8/2007 | Burnett |
| 2008/0109087 A1 * | 5/2008 | Durgin ........................ 623/23.65 |

* cited by examiner

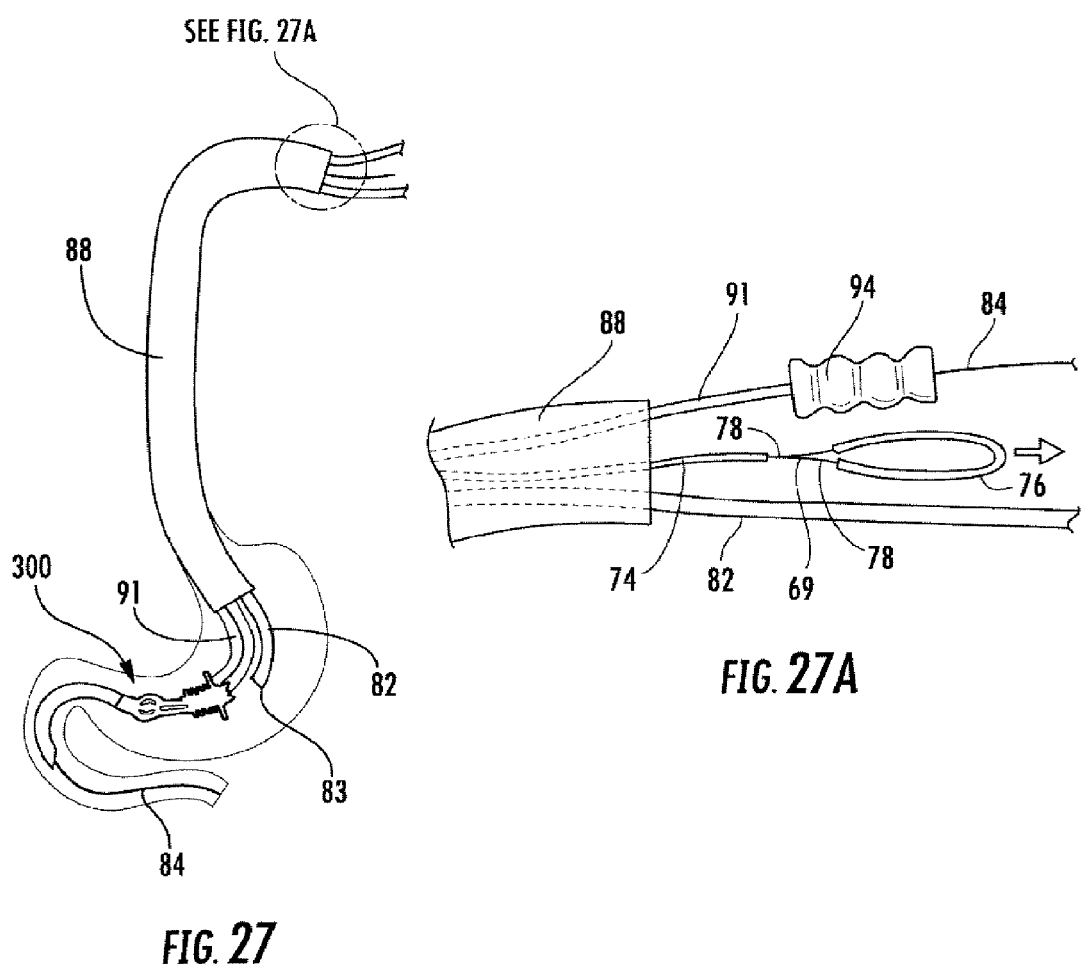

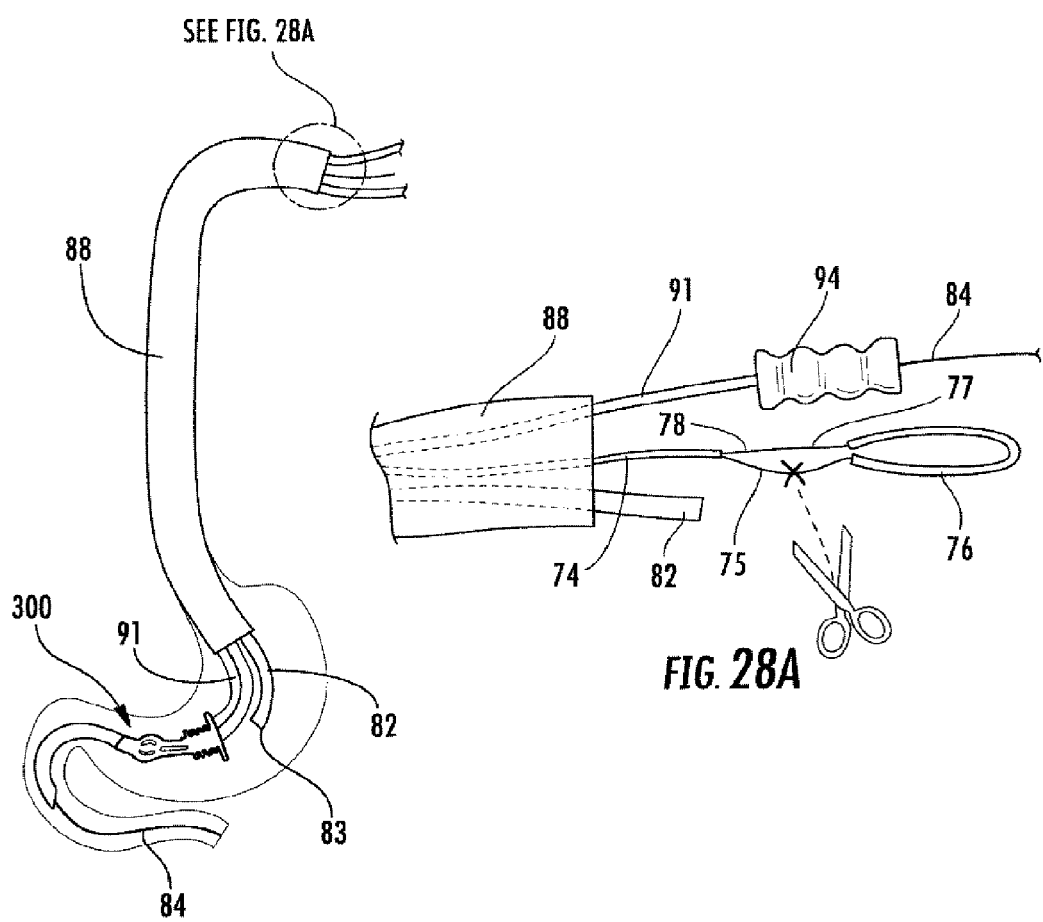

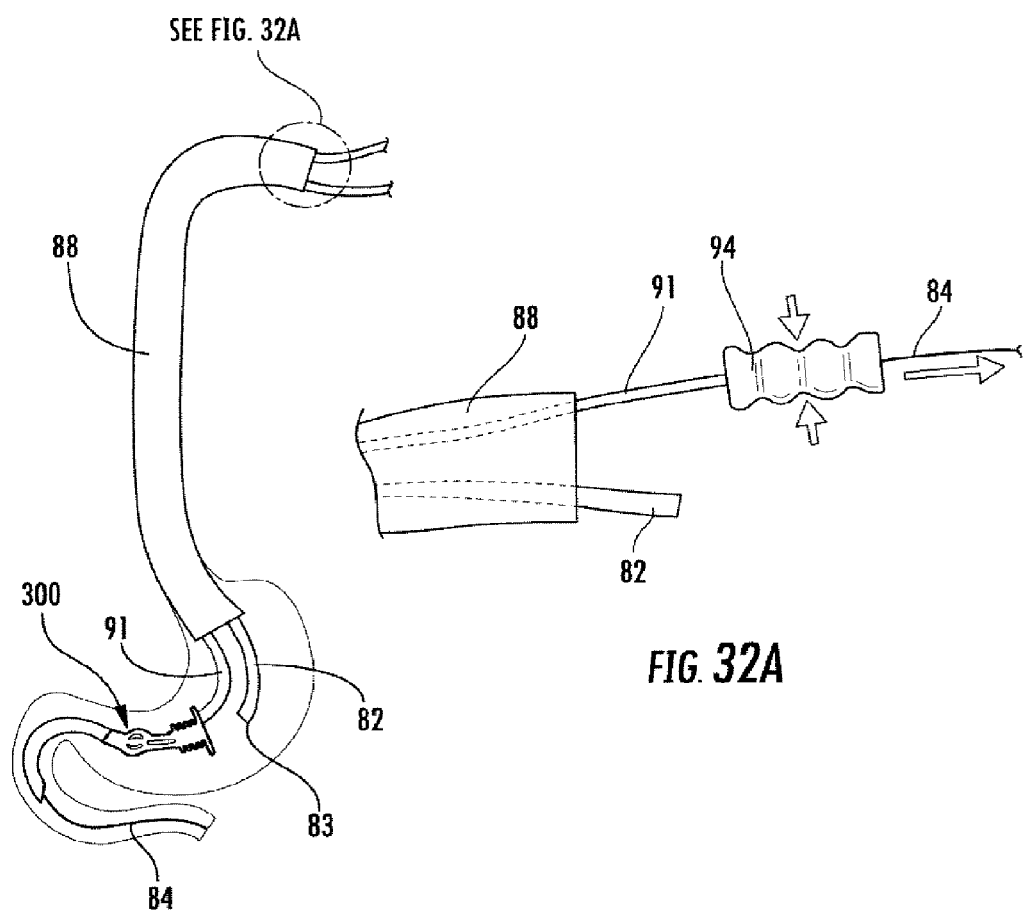

PYLORIC VALVE DEVICES AND METHODS

CROSS-REFERENCE TO RELATED APPLICATIONS

This application is a continuation of co-pending U.S. application Ser. No. 12/384,890 filed Apr. 9, 2009 which claims the benefit of the filing dates of U.S. Provisional Patent Application No. 61/123,472 filed Apr. 9, 2008, and entitled PYLORIC VALVE, and U.S. Provisional Patent Application No. 61/206,048 filed Jan. 27, 2009, and entitled PYLORIC VALVE DEVICES AND METHODS, the disclosures of which are hereby incorporated herein by reference.

FIELD OF THE TECHNOLOGY

The present invention relates to devices and methods of implanting the devices in the gastrointestinal ("GI") tract to aid in controlling obesity, and more particularly to pyloric valves and methods of implanting the pyloric valves in the pyloric region of the stomach to control the flow of chyme through the stomach.

BACKGROUND OF THE INVENTION

Obesity is a condition in which the natural energy reserve, stored in the fatty tissue of humans and other mammals, is increased to a point where it is associated with certain adverse health conditions. Although obesity is an individual clinical condition, it is increasingly viewed as a serious and growing public health problem. Excessive body weight has been shown to be a predisposition to various diseases, particularly cardiovascular diseases, diabetes mellitus type 2, sleep apnea and osteoarthritis.

The main treatment for obesity is to reduce body fat by ingesting fewer calories and increasing exercise. A beneficial side effect of exercise is to increase muscle, tendon, and ligament strength, which helps to prevent injury from accidents and vigorous activity. Diet and exercise programs produce an average weight loss of approximately 8% of total body mass (excluding results from those individuals who drop out of such programs). Not all dieters are satisfied with these results, but a loss of as little as 5% of body mass can create large health benefits. Much more difficult than reducing body fat is maintaining its absence. Eighty to ninety-five percent of those who lose 10% or more of their body mass through dieting regain their lost body mass within two to five years.

The body has systems that maintain its homeostasis, including body weight, at certain set points. Therefore, keeping weight off generally requires making exercise and healthy eating a permanent part of a person's lifestyle. Certain nutrients or chemicals, such as phenylalanine, are natural appetite suppressants which allow the body to reset its set point with regard to body weight. However, dieting, exercise, and/or appetite suppressants may not result in sufficient weight loss in patients with serious medical conditions.

An alternative mechanism for hunger suppression might require decreasing the rate of gastric emptying without the ingestion of chemicals in an effort to regulate satiety. It should be understood that the effects of regulating satiety may vary between individuals.

Partially undigested food in the GI tract is generally referred to as chyme. Satiety receptors are generally located all along the stomach. If chyme remains in the stomach for a longer period of time than it naturally would before flowing into the small intestine, the satiety receptors have a greater chance of being activated to signal the sensation of being satiated.

Therefore, a need exists for a device that is structured to inhibit the rate that chyme passes through the GI tract while allowing natural peristaltic action to occur. Such a device would, in effect, regulate satiety and control body mass, and thus obesity, through its implantation in the GI tract. Also, such a device implanted in the stomach and/or small intestine would enhance the ability of an overweight or obese patient to feel satiated so that the patient does not overeat, but rather eat less than normal.

There also exists a need for a novel method of implanting such a device in the pyloric region of the GI tract. Generally, such a device would enter the GI tract endoscopically and would pass through an endoscope in an unexpanded or compressed form. After the device has passed through the endoscope and is implanted in the region, the device preferably would expand to fit securely against tissue surrounding the region such that the position of the device is substantially maintained throughout the digestive process.

SUMMARY OF THE INVENTION

A first aspect of the present invention is a pyloric valve for inhibiting the flow of chyme through the pyloric region of the gastrointestinal tract comprising a blocking portion including at least one axially-aligned annular flange defining a central opening and having an outer circumference and a recess disposed in the outer circumference, and a support having a rim and a support surface, the rim being connected to the proximal-most of the at least one axially-aligned annular flange, the support having a nested position wherein the support surface is disposed within the central opening and an inverted position wherein the support surface is disposed away from the central opening.

In accordance with certain embodiments of this first aspect, the recesses of the at least one axially-aligned annular flange may be axially aligned. Each of the at least one axially-aligned annular flange may be connected to another through at least one strut. The at least one axially-aligned annular flange may further include at least one projection extending radially from the outer circumference. The support surface may define a convexity. The convexity may be open toward the proximal direction when the support is in the nested position. The convexity may be open toward the distal direction when the support is in the inverted position. The blocking portion and the support may together comprise a proximal portion, and the pyloric valve may further comprise an intermediate portion and a distal portion. The intermediate portion may include at least one flexible column and a part-spherical portion. The at least one flexible column may be connected to the proximal portion. The part-spherical portion may connect the at least one flexible column to the distal portion. The distal portion may include a sleeve. The sleeve may include a tubular surface having one or more apertures. The sleeve may include a beveled distal end. The pyloric valve may be constructed of silicon.

In accordance with further embodiments of this first aspect, a kit may be provided comprising the pyloric valve and an insertion system including a gastroscope, a fluoroscope, a guidewire, a first tube, a second tube larger in diameter than the first tube, and an over-tube larger in diameter than the second tube. A kit may be provided comprising the pyloric valve and a removal system including a gastroscope, a fluoroscope, an over-tube, and at least one of a snare, a grasper, and a pair of scissors.

A second aspect of the present invention is a method of inserting a pyloric valve for inhibiting the flow of chyme through the pyloric region of the gastrointestinal tract comprising the steps of providing a pyloric valve including a blocking portion and a support, the blocking portion having at least one axially-aligned annular flange defining a central opening and having an outer circumference and a recess disposed in the outer circumference, the support having a rim and a support surface, the rim being connected to the proximal-most of the at least one axially-aligned annular flange, the support having a nested position wherein the support surface is disposed within the central opening and an inverted position wherein the support surface is disposed away from the central opening, inserting the pyloric valve through a patient's esophagus and into the patient's stomach with the support in the inverted position, positioning the pyloric valve to a location adjacent to the patient's pyloric sphincter, and manipulating the support from the inverted position to the nested position.

In accordance with certain embodiments of this second aspect, the support surface may define a convexity, and the step of manipulating may include manipulating the support such that the convexity is changed from an orientation where it is open toward the distal direction to an orientation where it is open toward the proximal direction. The step of providing a pyloric valve may further include the blocking portion being a proximal portion, and the pyloric valve may further comprise an intermediate portion and a distal portion, the intermediate portion including at least one flexible column, and the distal portion including a sleeve, wherein the step of positioning may include positioning the intermediate portion substantially within the pyloric sphincter of the patient. The step of manipulating may include using a pulley system having a suture.

A third aspect of the present invention is a pyloric valve for inhibiting the flow of chyme through the pyloric region of the gastrointestinal tract comprising a blocking portion including a plurality of disc-shaped flanges connected in series, each of the plurality of disc-shaped flanges having an outer circumference and a recess disposed in the outer circumference, the blocking portion having a contracted position wherein the plurality of disc-shaped flanges is disposed in a stacked configuration and a resting position wherein the plurality of disc-shaped flanges is disposed in a linear configuration.

In accordance with certain embodiments of this third aspect, the recesses of the plurality of disc-shaped flanges may be axially aligned when the blocking portion is in the contracted position. Any one or more of the plurality of disc-shaped flanges may further include at least one projection extending radially from the outer circumference. The blocking portion may be a proximal portion, and the pyloric valve may further comprise an intermediate portion and a distal portion, the intermediate portion including at least one flexible column and a part-spherical portion, the at least one flexible column being connected to the proximal portion, and the part-spherical portion connecting the at least one flexible column to the distal portion. The distal portion may include a sleeve. The sleeve may include a tubular surface having one or more apertures. The sleeve may include a beveled distal end. The pyloric valve may be constructed of silicon.

In accordance with further embodiments of this third aspect, a kit may be provided comprising the pyloric valve and an insertion system including a gastroscope, a fluoroscope, a guidewire, a first tube, a second tube larger in diameter than the first tube, and an over-tube larger in diameter than the second tube. A kit may be provided comprising the pyloric valve and a removal system including a gastroscope, a fluoroscope, an over-tube, and at least one of a snare, a grasper, and a pair of scissors.

A fourth aspect of the present invention is a method of inserting a pyloric valve for inhibiting the flow of chyme through the pyloric region of the gastrointestinal tract comprising the steps of providing a pyloric valve including a blocking portion having a plurality of disc-shaped flanges connected in series, each of the plurality of disc-shaped flanges having an outer circumference and a recess disposed in the outer circumference, the blocking portion having a contracted position wherein the plurality of disc-shaped flanges is disposed in a stacked configuration and a resting position wherein the plurality of disc-shaped flanges is disposed in a linear configuration, inserting the pyloric valve through a patient's esophagus and into the patient's stomach with the blocking portion in the resting position, positioning the pyloric valve within the patient's pyloric sphincter, and manipulating the blocking portion from the resting position to the contracted position.

In accordance with certain embodiments of this fourth aspect, the step of providing a pyloric valve may further include the blocking portion being a proximal portion, and the pyloric valve may further comprise an intermediate portion and a distal portion, the intermediate portion including at least one flexible column, the distal portion including a sleeve, wherein the step of positioning may include positioning the intermediate portion substantially within the pyloric sphincter of the patient. Each of the plurality of disc-shaped flanges may further include a central aperture and a suture threaded through each successive aperture, and the step of manipulating may further include stacking the plurality of disc-shaped flanges in the contracted position by sliding at least one of the plurality of disc-shaped flanges distally along the suture.

A fifth aspect of the present invention is a pyloric valve for inhibiting the flow of chyme through the pyloric region of the gastrointestinal tract comprising a blocking portion including a disc-shaped inlet and a helical flange, the disc-shaped inlet having an outer circumference and a recess disposed in the outer circumference, and the helical flange extending along a longitudinal axis and having an outer edge and at least one recess disposed in the outer edge, the helical flange having a contracted position defining a contracted length and a contracted diameter and an extended position defining an extended length and an extended diameter, wherein the extended length is longer than the contracted length and the extended diameter is smaller than the contracted diameter.

In accordance with certain embodiments of this fifth aspect, the recesses of the disc-shaped inlet and the helical flange may be axially aligned when the helical flange is in the contracted position. The disc-shaped inlet may further include at least one projection extending radially from the outer circumference. The blocking portion may be a proximal portion, and the pyloric valve may further comprise an intermediate portion and a distal portion, the intermediate portion including at least one flexible column and a part-spherical portion, the at least one flexible column being connected to the proximal portion, and the part-spherical portion connecting the at least one flexible column to the distal portion. The distal portion may include a sleeve. The sleeve may include a tubular surface having one or more apertures. The sleeve may include a beveled distal end. The pyloric valve may be constructed of silicon.

In accordance with further embodiments of this fifth aspect, a kit may be provided comprising the pyloric valve and an insertion system including a gastroscope, a fluoroscope, a guidewire, a first tube, a second tube larger in diameter than the first tube, and an over-tube larger in diameter than the second tube. A kit may be provided comprising the pyloric valve and a removal system including a gastroscope, a fluoroscope, an over-tube, and at least one of a snare, a grasper, and a pair of scissors.

A sixth aspect of the present invention is a method of inserting a pyloric valve for inhibiting the flow of chyme through the pyloric region of the gastrointestinal tract comprising the steps of providing a pyloric valve including a blocking portion having a disc-shaped inlet and a helical flange, the disc-shaped inlet having an outer circumference and a recess disposed in the outer circumference, and the helical flange extending along a longitudinal axis and having an outer edge and at least one recess disposed in the outer edge, the helical flange having a contracted position defining a contracted length and a contracted diameter and an extended position defining an extended length and an extended diameter, wherein the extended length is longer than the contracted length and the extended diameter is smaller than the contracted diameter, inserting the pyloric valve through a patient's esophagus and into the patient's stomach with the helical flange is in the extended position, positioning the pyloric valve within the patient's pyloric sphincter, and manipulating the helical flange from the extended position to the contracted position.

In accordance with certain embodiments of this sixth aspect, the step of providing a pyloric valve may further include the blocking portion being a proximal portion, the pyloric valve may further comprise an intermediate portion and a distal portion, the intermediate portion including at least one flexible column, the distal portion including a sleeve, and the step of positioning includes positioning the intermediate portion substantially within the pyloric sphincter of the patient. The step of manipulating may include forcing the disc-shaped inlet against the helical flange.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 27 is a step in process of actuating the implant shown in FIG. 21 from its inverted position to its nested position using a pulley system.
FIG. 27a is close-up view of the step shown in FIG. 27.
FIG. 28 is the removal of the pulley system shown in FIG. 27.
FIG. 28a is close-up view of the step shown in FIG. 28.
FIG. 32 is still another step in the process of removing insertion equipment from the patient.
FIG. 32a is close-up view of the step shown in FIG. 32.

DETAILED DESCRIPTION

As used herein, when referring to parts of the body, the term "proximal" means closer to the heart and the term "distal" means more distant from the heart. The term "inferior"

means lower or bottom and the term "superior" means upper or top. The term "anterior" means towards the front part of the body or the face and the term "posterior" means towards the back of the body. The term "medial" means toward the midline of the body and the term "lateral" means away from the midline of the body.

Figure 1:
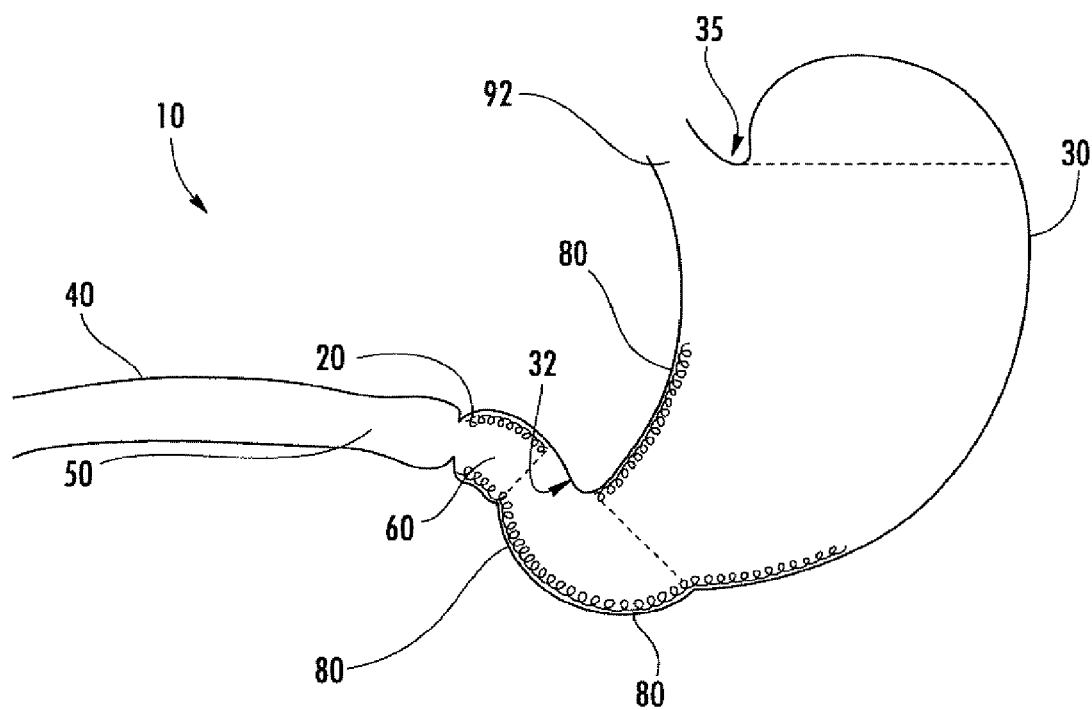
FIG. 1 is a view of a portion of a normal GI tract of a human.

Referring to the drawings, wherein like reference numerals refer to like elements, there is shown in FIG. 1 an example of a portion of a GI tract 10 of a human body. Two smooth muscle valves, or sphincters, contain the contents of the stomach within the stomach upon ingestion. They are the esophageal sphincter (not shown), found in the cardiac region above the antrum cardiacum, and the pyloric sphincter 20, disposed between the stomach 30 and the small intestine 40. Pyloric sphincter 20 is a strong ring of smooth muscle at the end of the pyloric canal that functions to help regulate the passage of chyme from stomach 30 to the duodenum 50. As shown in FIG. 1, the pyloric antrum 60 is located between stomach 30 and pyloric sphincter 20, or it can be said that pyloric antrum 60 is located proximally of pyloric sphincter 20. Therefore, duodenum 50 is located distally of pyloric sphincter 20.

Satiety receptors 80 are generally located all along the inside lining of stomach tissue. Partially undigested food in GI tract 10 is generally referred to as chyme. If chyme remains in the region of the stomach before flowing into small intestine 40, satiety receptors 80 have a greater chance of being activated, which enhances the ability of an overweight or obese patient to feel satiated and suppresses the desire to eat.

A pyloric valve or implant according to any of the below-described embodiments is preferably comprised of a polymeric structure that is compliant and generally flexible and bendable. Preferably, at least a portion of the implant is made of silicone. Some portions of the implant may be thicker than others for enhanced strength properties and to enhance the capability of the implant to resist the natural peristaltic action of GI tract 10. Alternatively, some portions of the implant may be thinner than others to allow for the material peristaltic actions of GI tract 10 to occur without the implant providing a counteractive force. Preferably, if a portion of the implant is bent or twisted during insertion, its polymeric structure will allow it to revert back to its resting or initial shape.

The one or more materials that comprise an implant according to the present invention are preferably selected for their ability to yield and flex during implantation and removal of the implant. These properties also protect the patient and the tissues and organs with which the implant comes into contact. The compliant nature of the implant allows its configuration to be manipulated during a surgical procedure, preferably in such a way that the implant tends to revert to its initial configuration. The implant may be made of shape memory material, such as nitinol or other known pliable polymeric materials, to allow for expansion back into its initial configuration. Any or all of the implant may be coated with Teflon to provide a smooth outer surface to reduce friction between the implant and the patient during implantation and removal.

An implant according to the present invention is structured to inhibit the rate that chyme passes through GI tract 10, thereby enhancing the ability of chyme to activate satiety receptors 80 and effectively enhance satiety in a patient. The implant is also preferably structured to reduce absorption. In particular, the implant is preferably structured to reduce the rate of gastric emptying such that obesity can be controlled by controlling satiety.

Certain components of an implant according to the present invention may be discussed as being attached or connected to one another. Preferably, the implant is constructed of one continuous piece and of one material, preferably silicone. However, two or more components of the implant may be manufactured separately and subsequently assembled. If assembled, components may be glued together using a silicone-based glue.

Preferably, an implant according to the present invention is configured to have a lesser or collapsed diameter during implantation and removal, and may expand to conform to the organs with which the implant comes into contact during and after implantation. These features are desirable for all components of the implant, whether manufactured together or separately.

Insertion and removal of an implant according to the present invention may require certain surgical tools. An insertion system 55 associated with the implant may include a guidewire 84, preferably of at least about 240 centimeters in length and preferably about 0.035 inches in diameter, at least one tube including a small tube 86, a medium tube 91, and an over-tube 88, and at least one device to aid in holding, pushing, or pulling the tubes, such as a handle. Preferably, small tube 86 includes a small tube handle 94 and medium tube 91 includes a medium tube handle 73. Small tube handle 94 and medium tube handle 73 may be connectable to form a single handle.

A removal system 65 associated with the implant may include a snare 98, a grasper 99, and a pair of scissors 90, which may be, for example, Olympus Scissors with a working length of approximately 165 centimeters and a channel size of approximately 2.8 millimeters, for example. Implantation and/or removal may further be aided by a fluoroscope 96 and/or a gastroscope 82. Gastroscope 82 is preferably approximately 9.8 millimeters in length, and preferably has approximately a 2.8 millimeter working channel and suitable viewing and recording equipment, for example. It will be understood that tools and components that are described as being passed through or inserted into gastroscope 82 are passed through or inserted into its working channel. A lubricant such as Surgilube or equivalent may be provided as needed to lubricate the implant and/or any of the associated surgical equipment.

Figure 2:
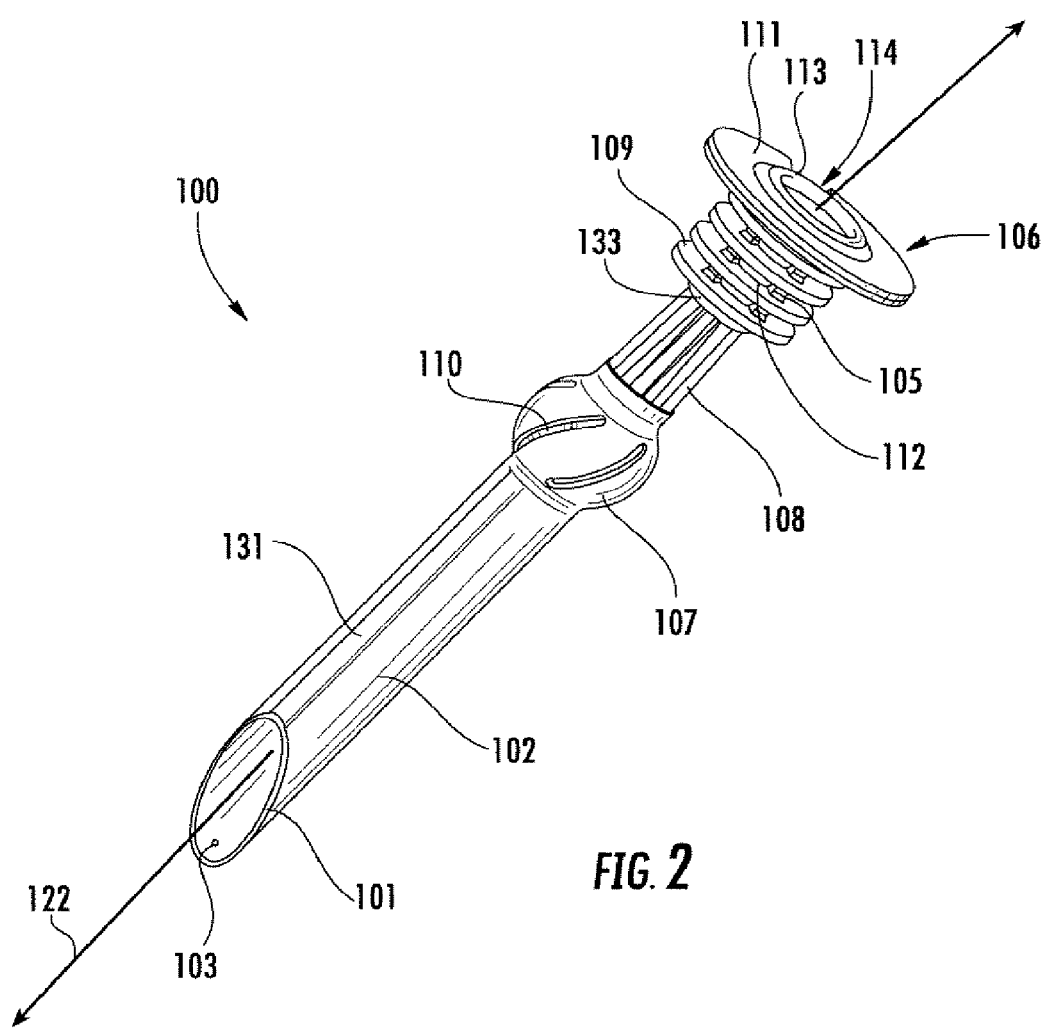
FIG. 2 is a perspective view of a "top hat" style implant in accordance with an embodiment of the present invention.

The following is a description of a "top hat" style implant. FIG. 2 depicts implant 100, which includes a sleeve 102, a duodenal sphere 107, at least one pyloric column 108, at least one axially-aligned annular flange 109, and a top portion 106. Sleeve 102 may be manufactured to any length according to a particular patient and/or surgical procedure, and includes at its distal end a beveled tip 101. Along its length, sleeve 102 may have one or more side holes 132 (not shown) which provide further access for chyme to enter sleeve 102.

Sleeve 102 is generally disposed along a longitudinal axis 122 of implant 100. A rib 131 is disposed along sleeve 102 and is preferably substantially parallel to longitudinal axis 122, though rib 131 may extend only partially along sleeve 102 and may take on a curved or other type of orientation with respect to longitudinal axis 122. Rib 131 may be comprised of silicone and additionally may include a radiopaque material, such as barium, so that rib 131 may be detected by fluoroscope 96. Rib 131 may be provided as a separate component and later attached to sleeve 102, or rib 131 may essentially be the overlapping seam formed during the manufacture of sleeve 102 when a flat piece of material is rolled into a tubular shape. In such a configuration, sleeve 102 may be comprised of a homogenous material attached by a radiopaque glue. Of course, as rib 131 is primarily used as an aid during implantation and/or removal of implant 100, rib 131 need not necessarily be included in this or any other embodiment according to the present invention.

Located on sleeve 102 adjacent to beveled tip 101 is a hole 103 that is preferably of a smaller diameter than the outer diameter of small tube 86. Small tube 86 is utilized in order to maintain the length of sleeve 102 by extending small tube 86 through sleeve 102 up to and against hole 103. Small tube 86 is otherwise too flimsy to translate a push force from the surgeon to implant 100.

Sleeve 102 is connected at its proximal end to duodenal sphere 107, which may include at least one slot 110 to enhance its flexibility and/or to provide additional means for the passage of chyme into sleeve 102. Slot 110 is angled with respect to a longitudinal axis 122 of implant 100, though any orientation of slot 110 with respect to longitudinal axis 122 would suffice. Slot 110 may also be shaped as any other geometrical figure, such as a circle, ellipse, quadrilateral, etc. Although more clearly shown in FIGS. 4-6 with respect to an implant 200, duodenal sphere 107 includes a boss 138 which is disposed within sleeve 102. Boss 138 is connected to sleeve either integrally or through bonding, and includes a passage 139 oriented along an axis that is preferably substantially parallel to longitudinal axis 122. Passage 139 preferably has an internal diameter greater than the external diameter of small tube 86, but smaller than the external diameter of medium tube 91.

Attached to the proximal end of duodenal sphere 107 is the at least one pyloric column 108, which may be cylindrical or any other type of prismic shape. Preferably, implant 100 includes three or more pyloric columns 108, which are attached to the at least one flange 109, or blocking member, through a button 133. Button 133 is preferably comprised of a material having a greater rigidity than the rest of implant 100, and may either be co-molded into implant 100 or assembled afterward as a separately manufactured component. Button 133 is configured similarly to a conventional button, being disc-shaped and having two or more bores 134 (not shown). Button 133 may be disposed within or adjacent to the distal-most flange 109.

Each flange 109 is substantially annularly shaped and defines an outer circumference and a central opening or hole. When two or more flanges 109 are provided, such may be connected by at least one strut 105. Struts 105 may, as depicted, be aligned to form a more formidable connection between flanges 109. It is also contemplated that struts 105 may be spaced circumferentially about each flange 109 such that they are not necessarily aligned along any axis parallel to longitudinal axis 122 of implant 100. Flanges 109 may have identical or varying outer diameters, and due to their composition, may flex and bend during positioning of implant 100 in stomach 20. Flanges 109 may also bend or flex due to natural peristaltic action of stomach 20 during contact with surrounding stomach tissue. It should be understood by one of ordinary skill in the art that flanges 109 may be of any configuration that allows flanges 109 to be connected to one another in a generally parallel and stacked configuration while allowing implant 100 to be positioned as described below. Each of flanges 109 includes a recess 114 which is preferably aligned along a recess axis 135 that is preferably substantially parallel to longitudinal axis 122, though recesses 114 need not be aligned in a parallel manner. Recesses 114 are configured to allow a tube, such as small tube 86 and/or medium tube 91, to pass therethrough and along flanges 109 without substantially changing the diametric size of implant 100 during insertion and removal.

Top portion 106, which is a support, includes a narrow end 112 and an inlet 111, which is essentially the proximal-most flange. Inlet 111 is substantially annular with an outer diameter that may be greater than that of any other flange 109. Narrow end 112, which is a support surface, connects with inlet 111 at an inner rim 113. Narrow end 112 may be manipulated to be disposed either distally of inlet 111 within the central openings of flanges 109 (as shown) or proximally of inlet 111 and away from the central openings of flanges 109, such that top portion 106 is in a nested or inverted position, respectively. The nested position is essentially a mirror image of the inverted position, with the plane of symmetry being essentially inlet 111. Stated another way, the narrow end 112, or support surface, is of a convex nature, wherein the open portion, or convexity, is open toward the proximal direction when the support is in the nested position. Similarly, the convexity of the narrow end 112, or the support surface, is open toward the distal direction when the support is in the inverted position.

Top portion 106 is included to provide reinforcement to the at least one flange 109. While implant 100 is comprised of a material that flexes and bends during implantation and removal, a more rigid composition is desired after implantation such that implant 100 will maintain its implanted position and thus properly reduce the flow of chyme through GI tract 10. Therefore, when top portion 106 is disposed in its nested position, it supports and provides a "backbone" for flanges 109. The inverted position of top portion 106 is thusly advantageous for implantation and removal in that implant 100 is in a more flexible state so as to yield more willingly to the patient's body tissue. Top portion 106 may be actuated between its nested and inverted positions from either outside or within the patient.

As flanges 109 act to control or inhibit the flow of chyme between stomach 30 and duodenum 50, the flow of gasses and other stomach fluids is similarly inhibited. Along with the normal peristaltic action of the surrounding tissue, such gasses may cause a buildup of pressure that may tend to force implant 100 in a distal or proximal direction. Recesses 114 aid in relieving such pressure between stomach 30 and duodenum 50 when implant 100 is fully inserted by allowing such gasses to pass through recesses 114. It is contemplated that recesses 114 may be staggered circumferentially about flanges 109 without compromising the ability of recesses 114 to reduce pressure.

Figure 4:
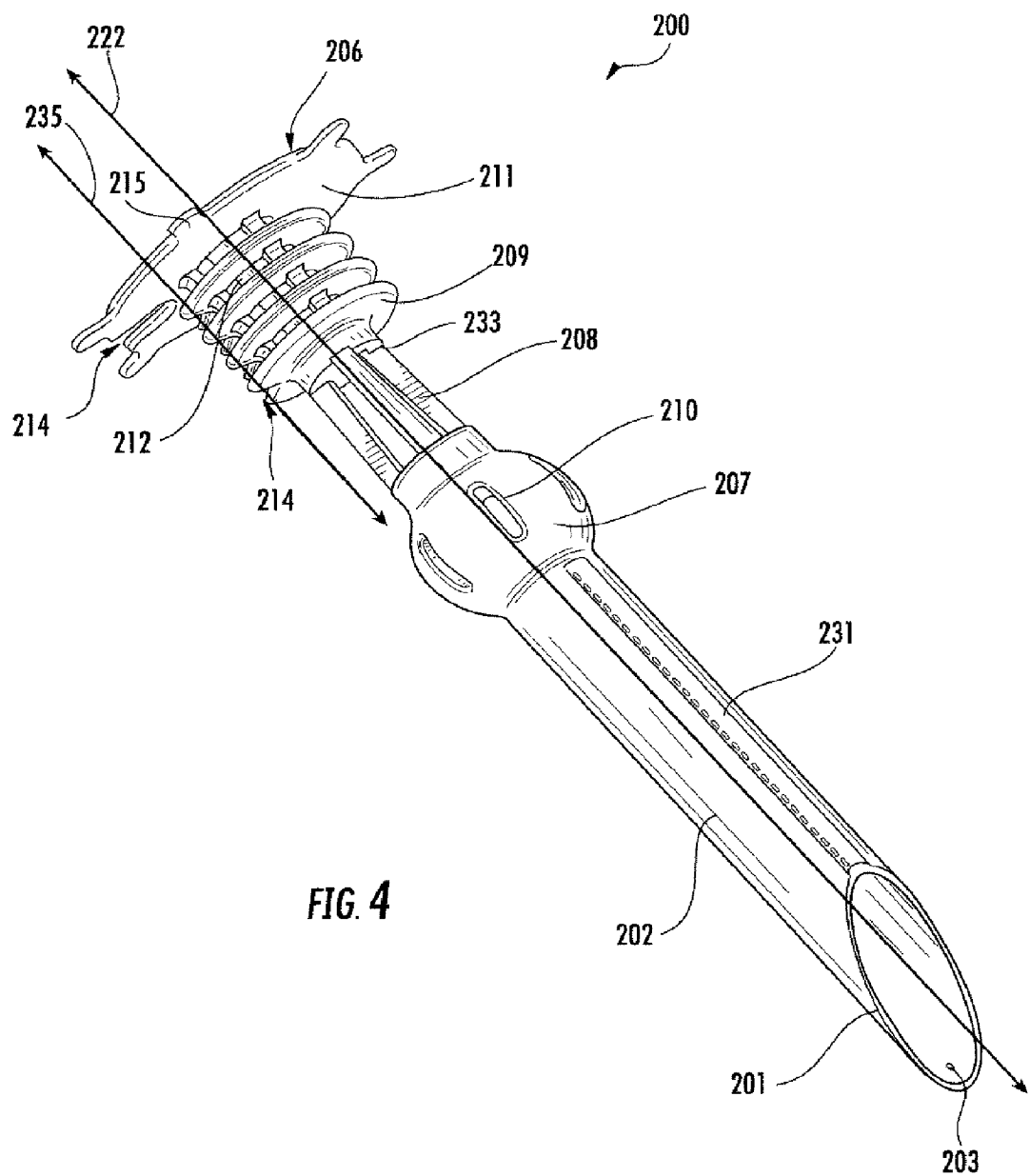
FIG. 4 is a perspective view of a "top hat" style implant according to another embodiment of the present invention.
Figure 5:
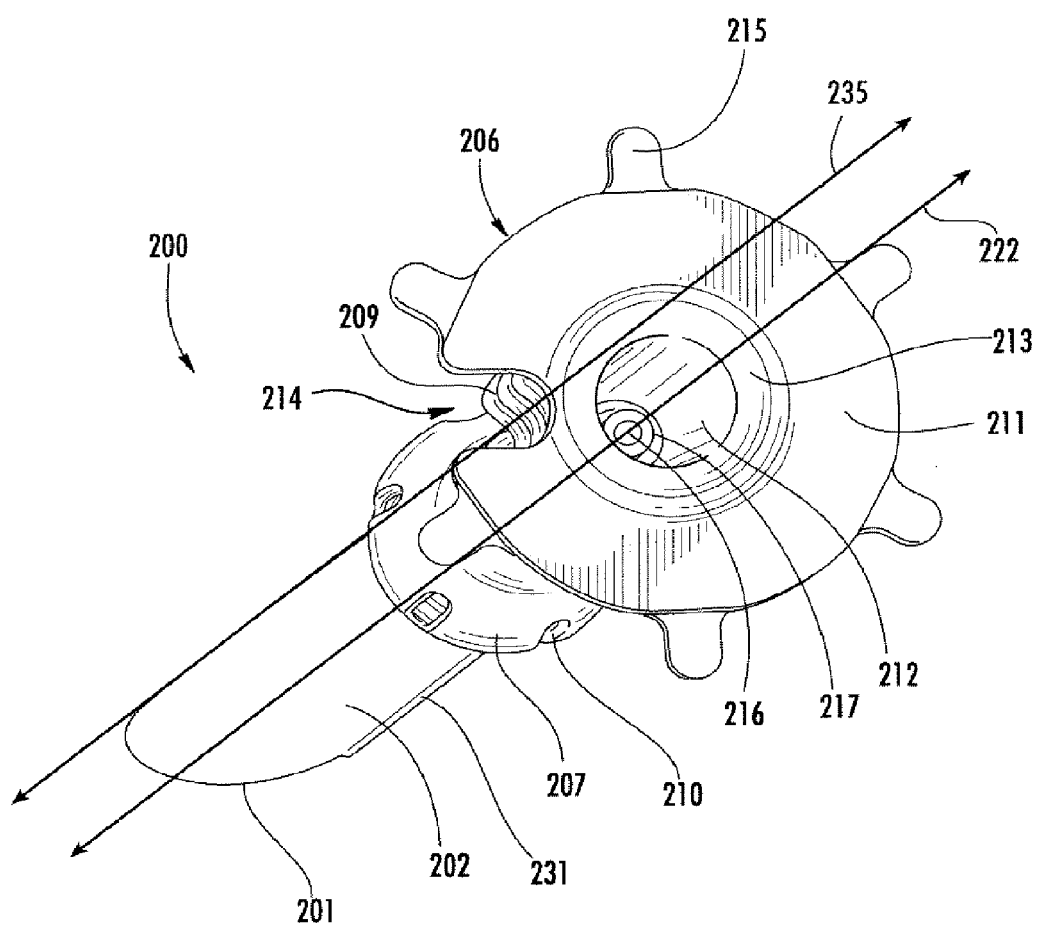
FIG. 5 is a perspective view of a proximal end of the implant shown in FIG. 4.
Figure 6:
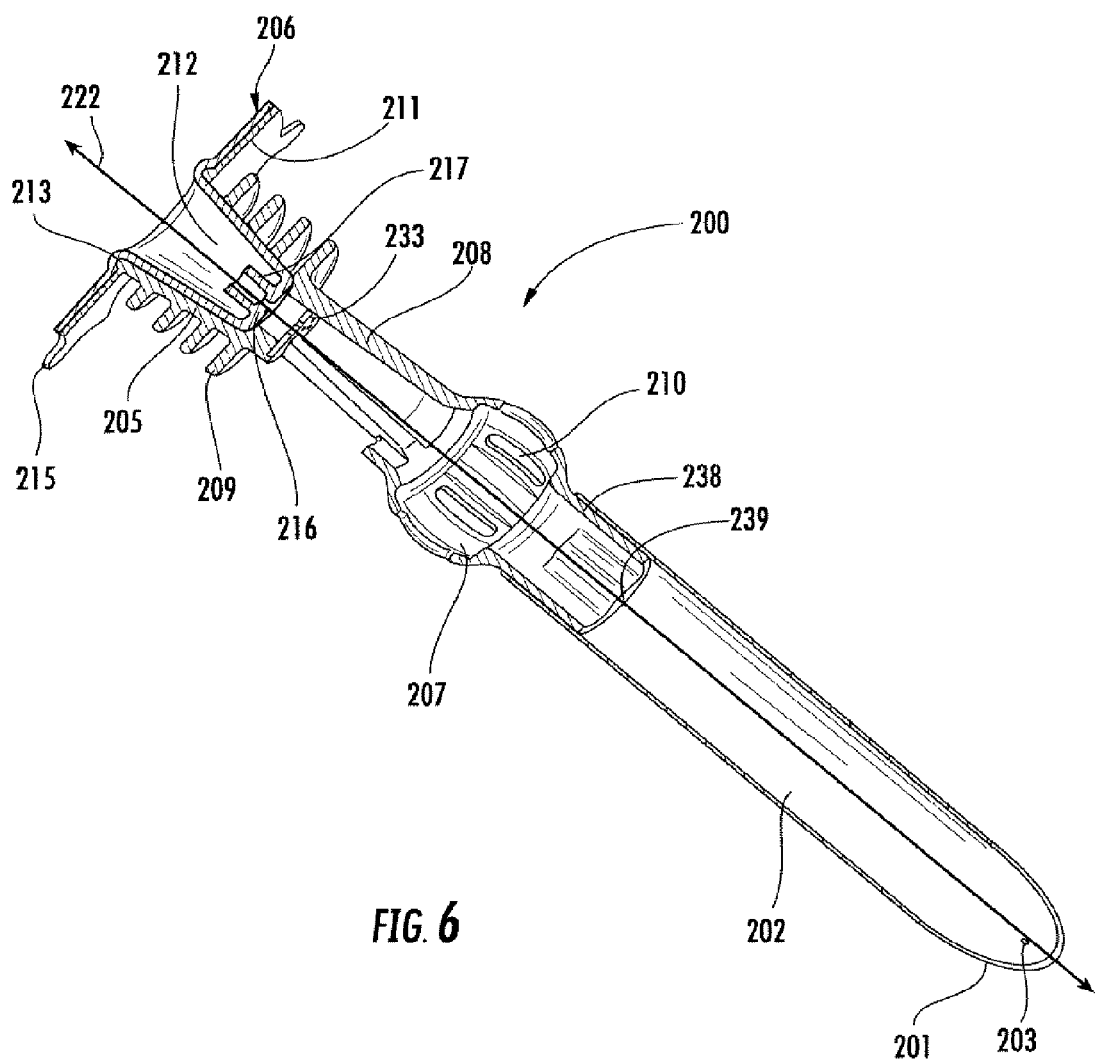
FIG. 6 is a sectional view of the implant shown in FIG. 4.

Another embodiment of implant 100 is depicted in FIGS. 4-6 as implant 200, with like elements referenced by like numbers. Inlet 211 of top portion 206 includes at least one projection 215 spaced circumferentially about its outer diameter. Projections 215 may aid in assembly of implant 200, and may be removed prior to insertion. Slots 210 of duodenal sleeve 207 are substantially parallel to longitudinal axis 222 of implant 200, as opposed to being slanted with respect thereto, as in implant 100. Narrow end 212 is more clearly shown to include an aperture 216 and an extension 217. Aperture 216 is disposed at the end of narrow end 212 opposite inlet 211. Extension 217 is cylindrically shaped and extends proximally from narrow end 212. Aperture 216 and extension 217 form a continuous through hole.

Figure 3:
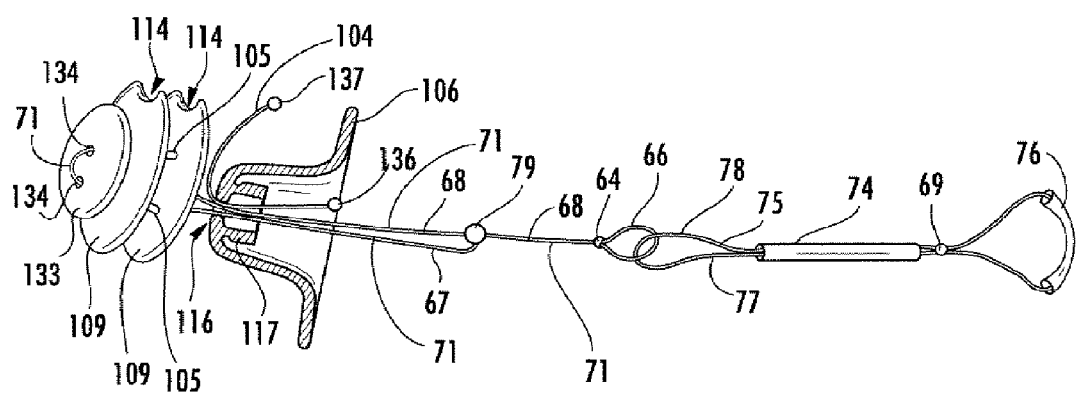
FIG. 3 is a perspective view of a pulley system utilized with the proximal end of the implant shown in FIG. 2.

With reference to implant 100 and as shown in FIG. 3, a pulley system 72 is utilized to actuate or manipulate top portion 106 between its nested and inverted positions. It will be understood that in FIG. 3, certain elements are exaggerated in size and certain others are omitted for clarity. Pulley system 72 preferably includes a bead 79, a bead suture 71, a gripping suture 78, a sheath 74, and a grip 76. Bead suture 71 includes a first end 67 attached to bead 79, and a second end 68 that extends through bead 79 such that bead 79 is slidable along bead suture 71. Bead 79 is disposed proximally of aperture 116 and is dimensioned not to allow for passage therethrough. Second end 68 of bead suture 71 forms a loop 66 which is tied to the adjacent bead suture 71 to form a bead suture knot 64, which is disposed proximally of bead 68 and dimensioned not to allow for passage therethrough. Bead suture knot 64 is preferably substantially anchored along bead suture 71.

With respect to implant 100, bead suture 71 is threaded distally through one bore 134 of button 133 and then proximally through another bore 134 of button 133. Both first end 67 and second end 68 extend proximally through aperture 116. Therefore, when second end 68 of bead suture 71 is pulled proximally, first end 67, and thus bead 79, is moved distally. Likewise, when either first end 67 or bead 79 is pulled proximally, second end 68 is moved distally. Button 133 thusly allows bead suture 71 to act as a pulley.

Gripping suture 78 includes a first end 75 and a second end 77, and is disposed through loop 66 of bead suture 71. First end 75 and second end 77 each extend proximally from loop 66 and through sheath 74, which extends from a point proximal of loop 66 to the exterior of the patient's mouth 70. First end 75 and second end 77 each extend proximally from sheath 74. One of first end 75 and second end 77 passes through grip 76 and is tied to the other to form a gripping suture knot 69 that is preferably substantially anchored at a point along gripping suture 78. Gripping suture knot 69 is preferably dimensioned such that it may be disposed within sheath 74.

Figure 21:
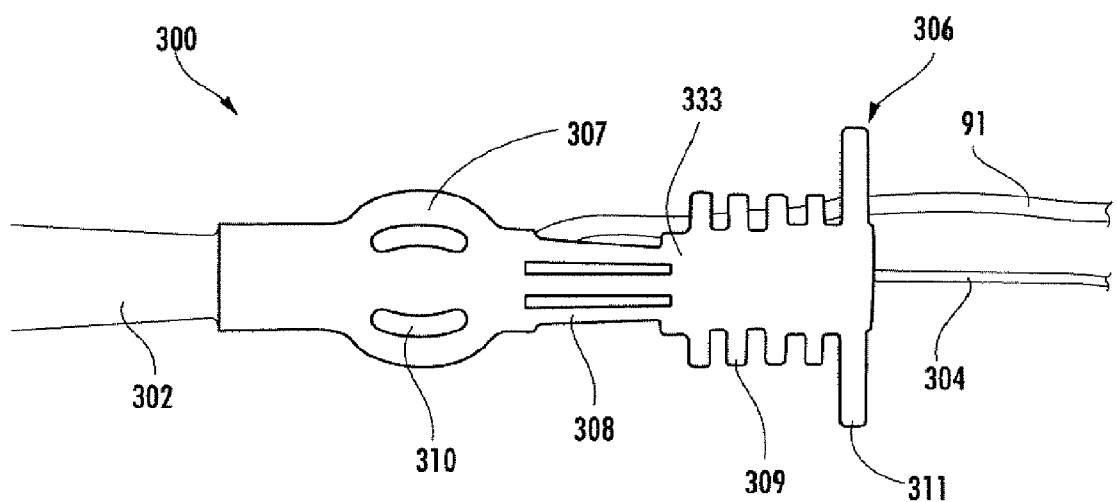
FIG. 21 is a "top hat" style implant in a nested position.
Figure 22:
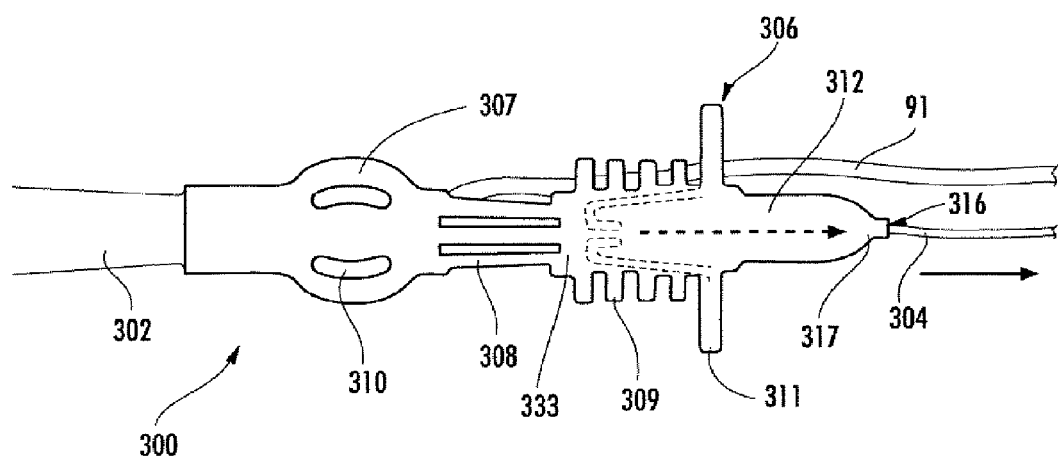
FIG. 22 is the implant shown in FIG. 21 in an inverted position.

Implant 100 is preferably manufactured and provided for insertion with top portion 106 in its inverted position, but may alternatively be prepared for insertion by way of an actuation suture 104 (shown in FIG. 3) threaded through aperture 116. Actuation suture 104 includes a proximal anchor 136 and a distal anchor 137 located proximally and distally, respectively, of aperture 116 along actuation suture 104. Both proximal anchor 136 and distal anchor 137 are dimensioned not to allow for passage through aperture 116. If top portion 106 is in the nested position prior to insertion, actuation suture 104 may be pulled proximally, whereby distal anchor 137 contacts top portion 106 adjacent aperture 116 and manipulates top portion 106 into its inverted position, as shown in FIGS. 21-22 with reference to a similar implant 300 having like elements to those described above with respect to implants 100 and 200. Actuation suture 104 is preferably relatively short compared to the length of top portion 106 and may either be removed or may remain after implantation of implant 100.

Figure 23:
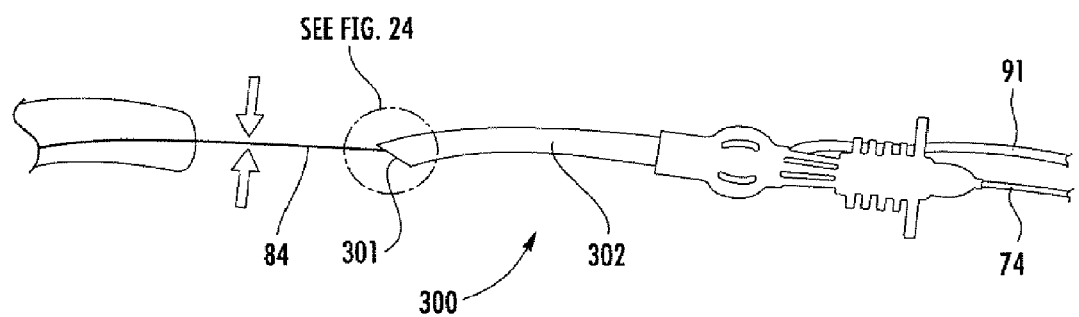
FIG. 23 is view of the guidewire being threaded through the implant shown in FIG. 22.
Figure 24:
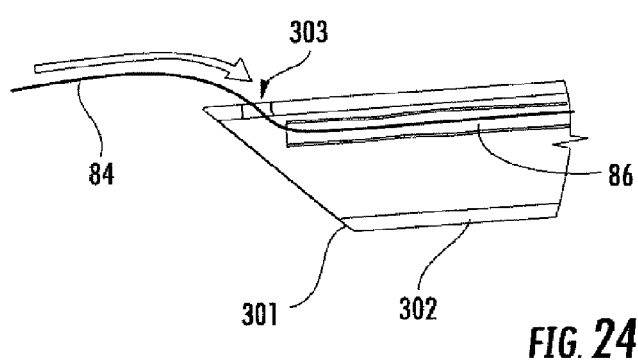
FIG. 24 is close-up sectional view of the guidewire being threaded through the distal end of the implant shown in FIG. 22.

Implant 100 is also preferably provided for insertion preassembled with the necessary insertion tools and instruments. Small tube 86 is preferably threaded along the at least one recess 114, between two of the pyloric columns 108, through duodenal sphere 107, through passage 139 in boss 138, and finally into sleeve 102. Passage 139 should be configured such that small tube 86 encounters friction therewithin, and a force is required to insert and/or remove small tube 86 from passage 139 which is greater than the forces that will generally be encountered during implantation and removal from the surrounding tissue. This helps small tube 86 to be stabilized within implant 100 in a proximal-distal direction. In this position, distal end 87 of small tube 86 is disposed adjacent to hole 103, as shown in FIG. 23. Small tube 86 may not be passed through hole 103, as the diameter of hole 103 is smaller than the outer diameter of small tube 86. Small tube 86 should be flexible, yet rigid enough to provide sleeve 102 with a "backbone" during the insertion of implant 100. As implant 100 and sleeve 102 are designed to be flexible in nature, small tube 86 is relatively less flexible and helps sleeve 102, and for that matter, the proximally-located components of implant 100, to substantially maintain its proximal-distal length during implantation.

Further in the preassembly, medium tube 91 is preferably threaded over and along small tube 86. Therefore, medium tube 91 is passed along the at least one recess 114, between two of the pyloric columns 108, through duodenal sphere 107, and up to the proximal end of passage 139. A distal end 95 of medium tube 91, having an outer diameter larger than the inner diameter of passage 139, is thusly disposed against boss 138 adjacent to passage 139 and may not be passed through passage 139. Small tube handle 94 and medium tube handle 73 are preferably connected, though such a connection is not necessary or required. As shown in FIG. 23, guidewire 84 is inserted through hole 103 and a distal end 87 of small tube 86, and advanced proximally through the full length of small tube 86 until guidewire 84 exits a proximal end 85 thereof and small tube handle 94.

The following describes a method of inserting a "top hat" style implant. FIGS. 18-40 depict a method of inserting an implant 300, having like elements to those described above with respect to implants 100 and 200. Implant 300 enters and exits the patient through esophagus 92 and is ultimately positioned in its operative state, wherein the at least one pyloric column 308 is adjacent to pyloric sphincter 20.

Figure 18:
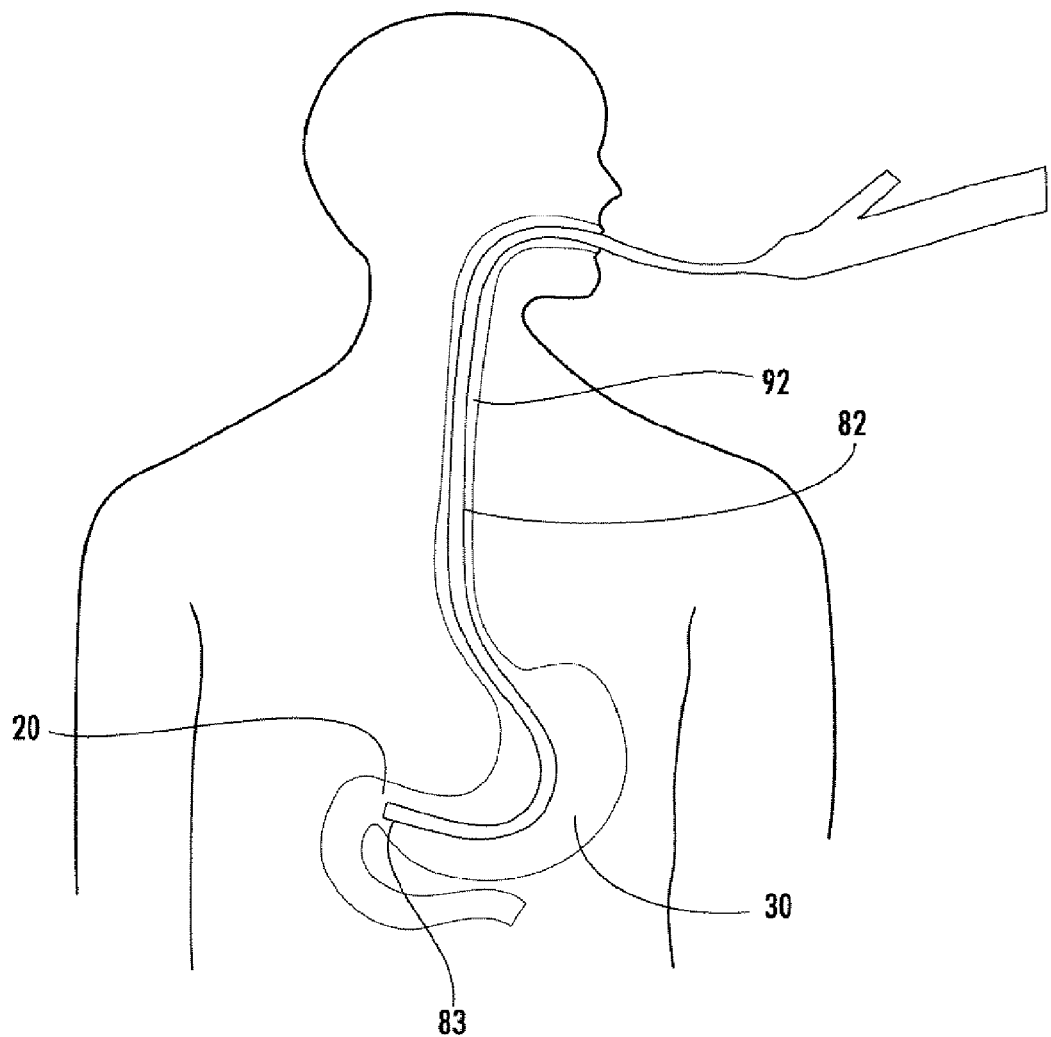
FIG. 18 is a gastroscope positioned through the esophagus of a patient with its distal end positioned adjacent to a pyloric sphincter.
Figure 19:
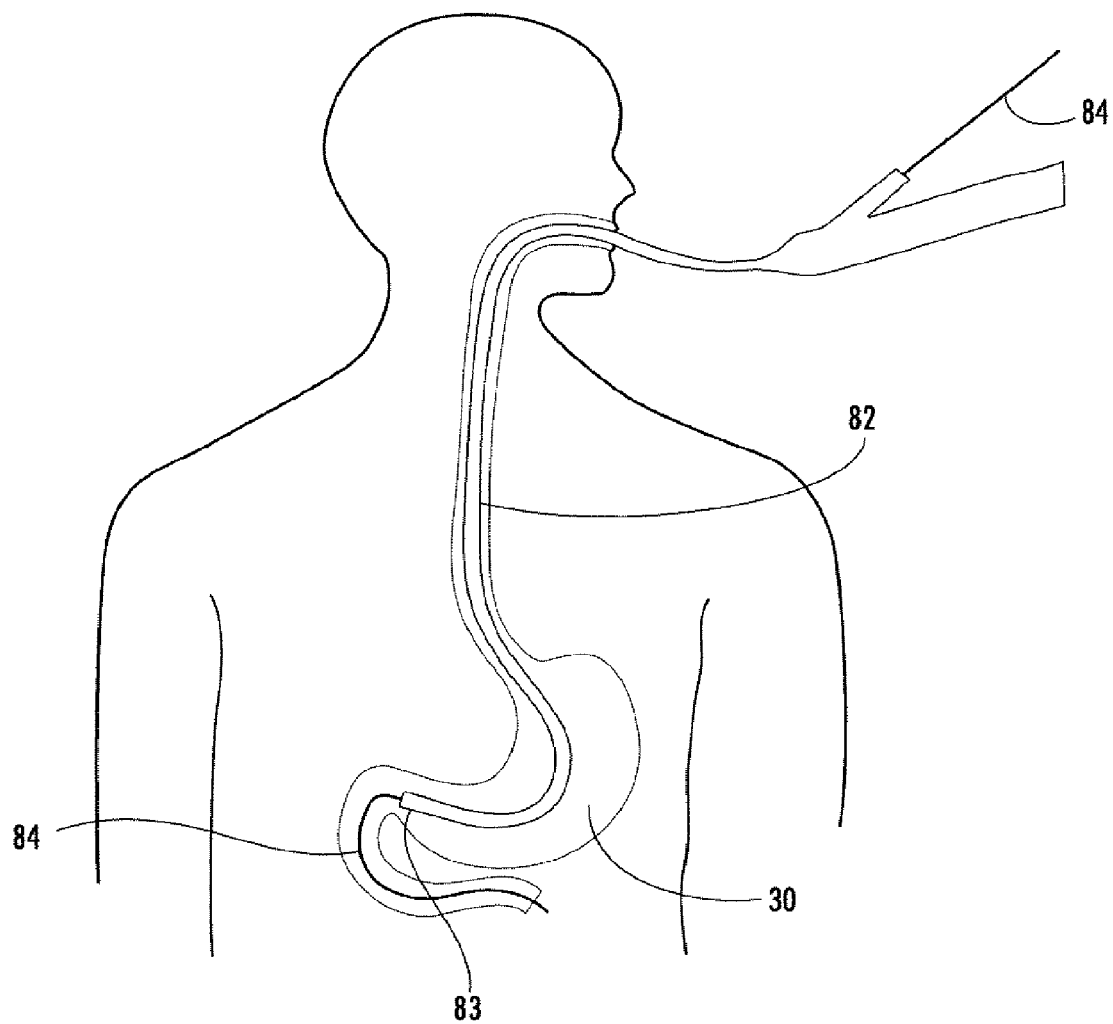
FIG. 19 is a guidewire positioned through the gastroscope shown in FIG. 18.
Figure 20:
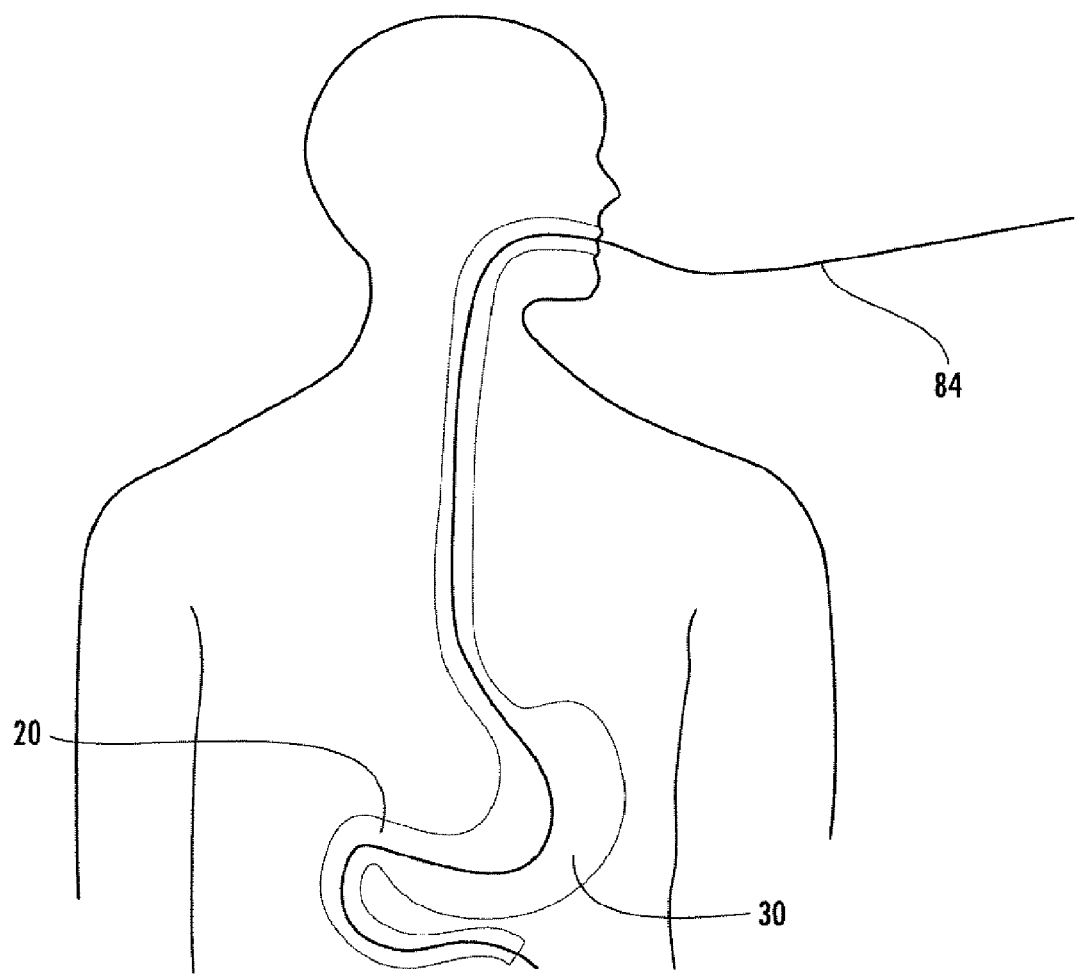
FIG. 20 is the guidewire shown in FIG. 19 properly positioned within the patient.

Initially, gastroscope 82 is lubricated, inserted into patient's mouth 70, and fed through esophagus 92 and the gastroesophageal ("GE") junction 35 into stomach 30, as shown in FIG. 18. Gastroscope 82 should ultimately be positioned such that its distal end is adjacent to pyloric sphincter 20. Preferably, a hydrophilic coating of guidewire 84 is hydrated and inserted through gastroscope 82, as shown in FIG. 19. Guidewire 84 is passed through pyloric sphincter 20, which may be aided by manipulation of gastroscope 82. It may also be beneficial to pass a distal end 83 of gastroscope 82 through pyloric sphincter 20 in order to maneuver guidewire 84 through same. There should preferably be at least about 30-40 centimeters of the length of guidewire 84 passed distally through pyloric sphincter 20 and into small intestine 40 so that any further movement of guidewire 84 during the insertion procedure does not result in the accidental removal of the distal end of guidewire 84 to a position proximal of pyloric sphincter 20. Of course, the length of guidewire 84 that should preferably be passed distally through pyloric sphincter 20 may vary according to different patients and/or procedures and may be less or more than 30-40 centimeters. After guidewire 84 is appropriately positioned, gastroscope 82 is removed from the patient. Fluoroscope 96 may then be used to check the positioning of guidewire 84, which should be situated as shown in FIG. 20.

With implant 300 is in its inverted position, implant 300 is thoroughly lubricated. Implant 300, small tube 86, and medium tube 91 are moved distally along guidewire 84 until implant 300 is positioned to be advanced down esophagus 92. Again, it is noted that during this procedure care must be taken not to pull guidewire 84 proximally out of small intestine 40.

Figure 25:
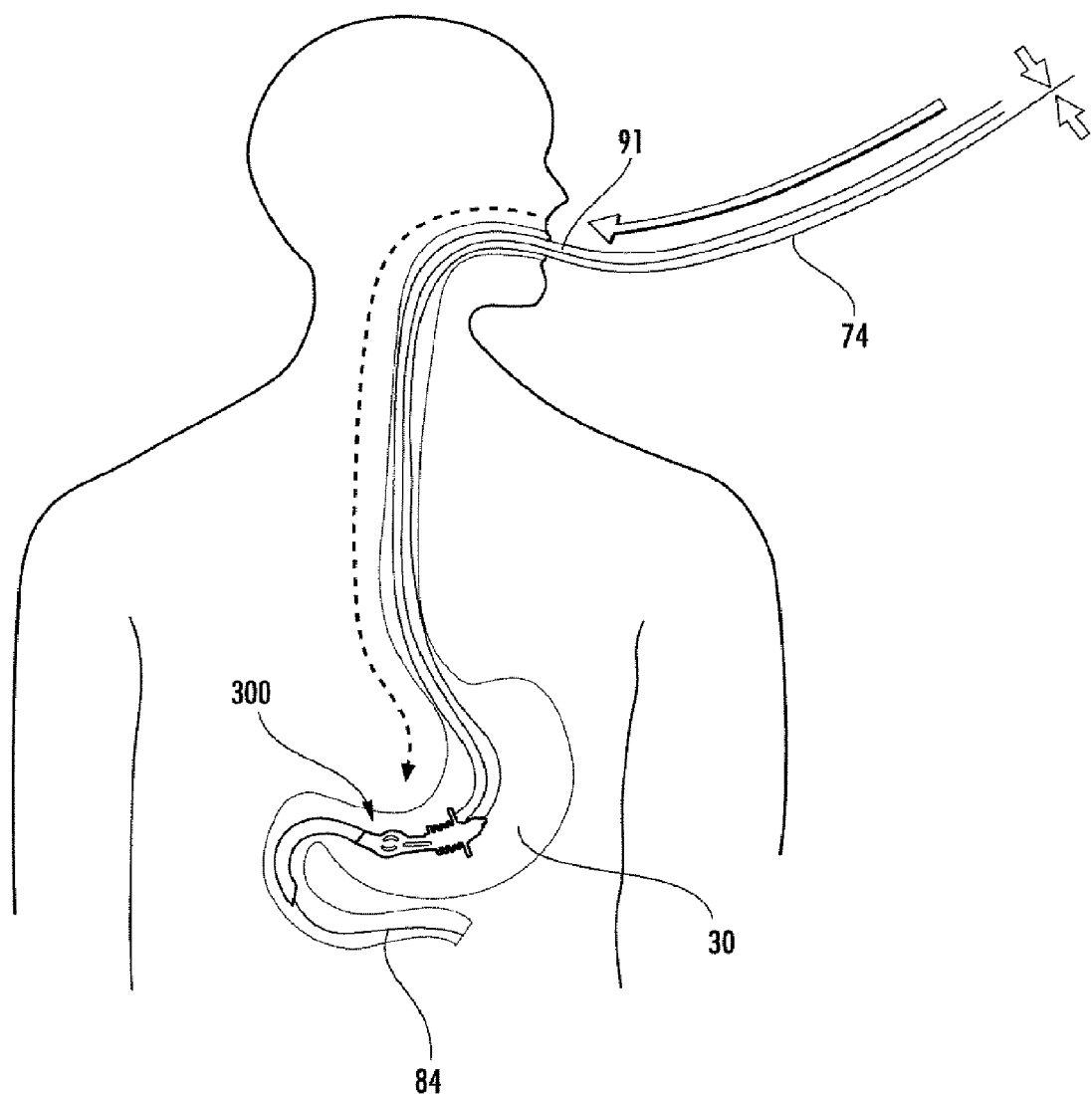
FIG. 25 is the implant shown in FIG. 21 being positioned in the patient's stomach.
Figure 26:
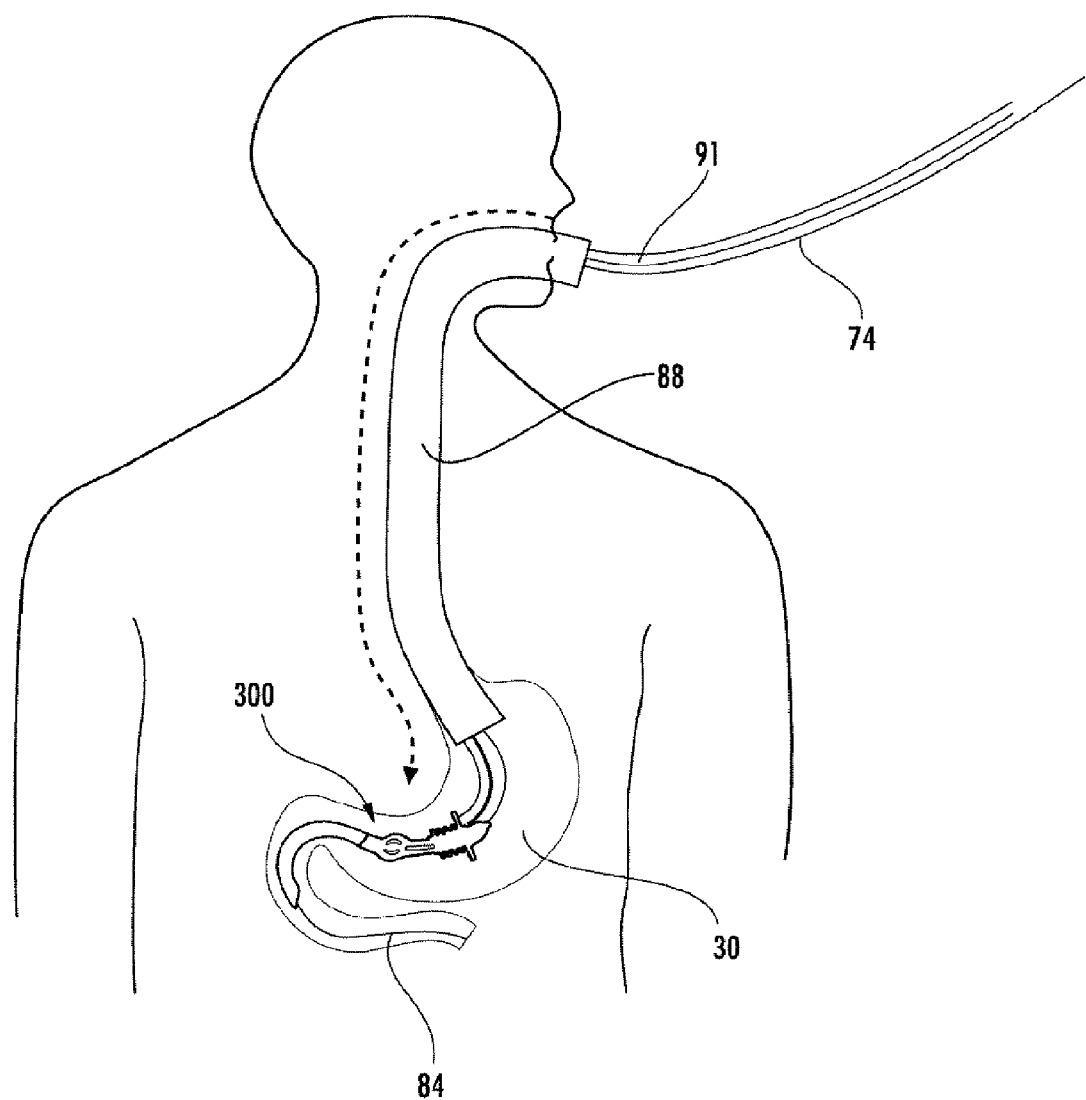
FIG. 26 is an over-tube being positioned through the esophagus and adjacent the implant shown in FIG. 21.
Figures 29, 29A:
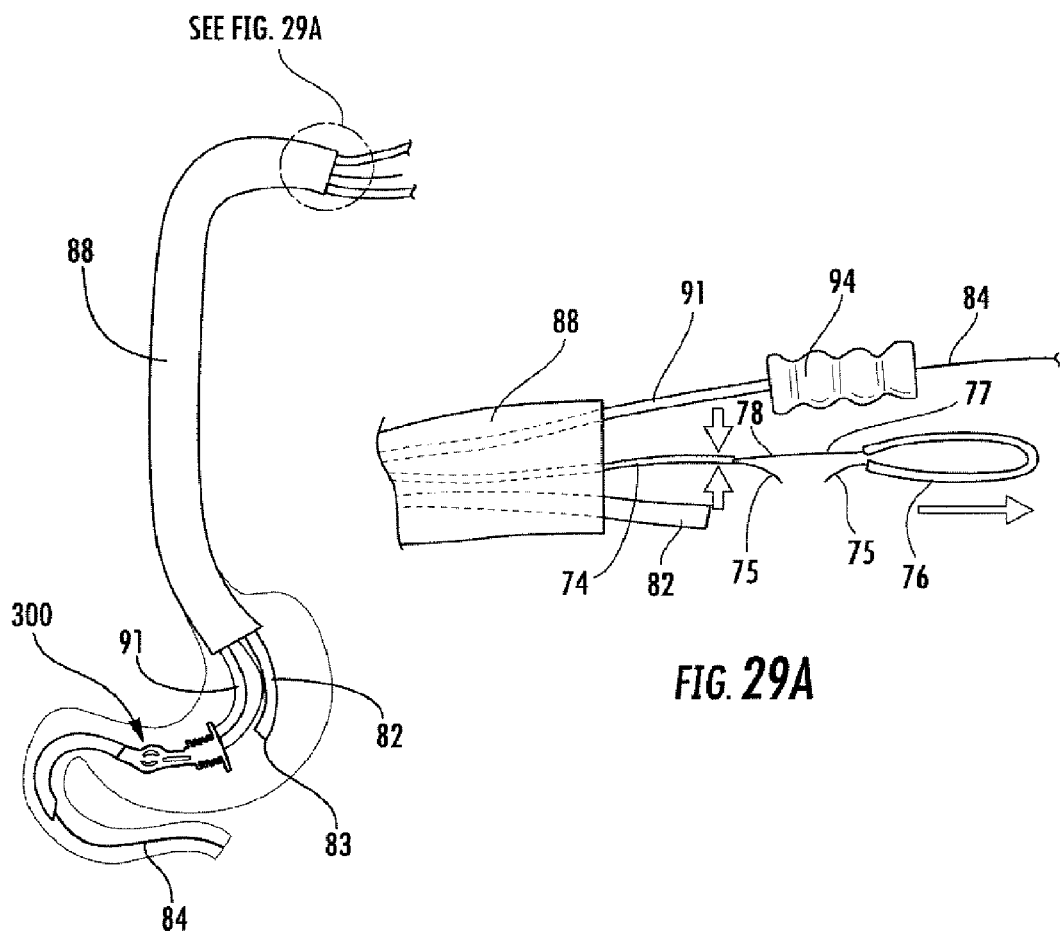
FIG. 29 is a step in the process of removing insertion equipment from the patient.
FIG. 29a is close-up view of the step shown in FIG. 29.
Figures 30, 30A:
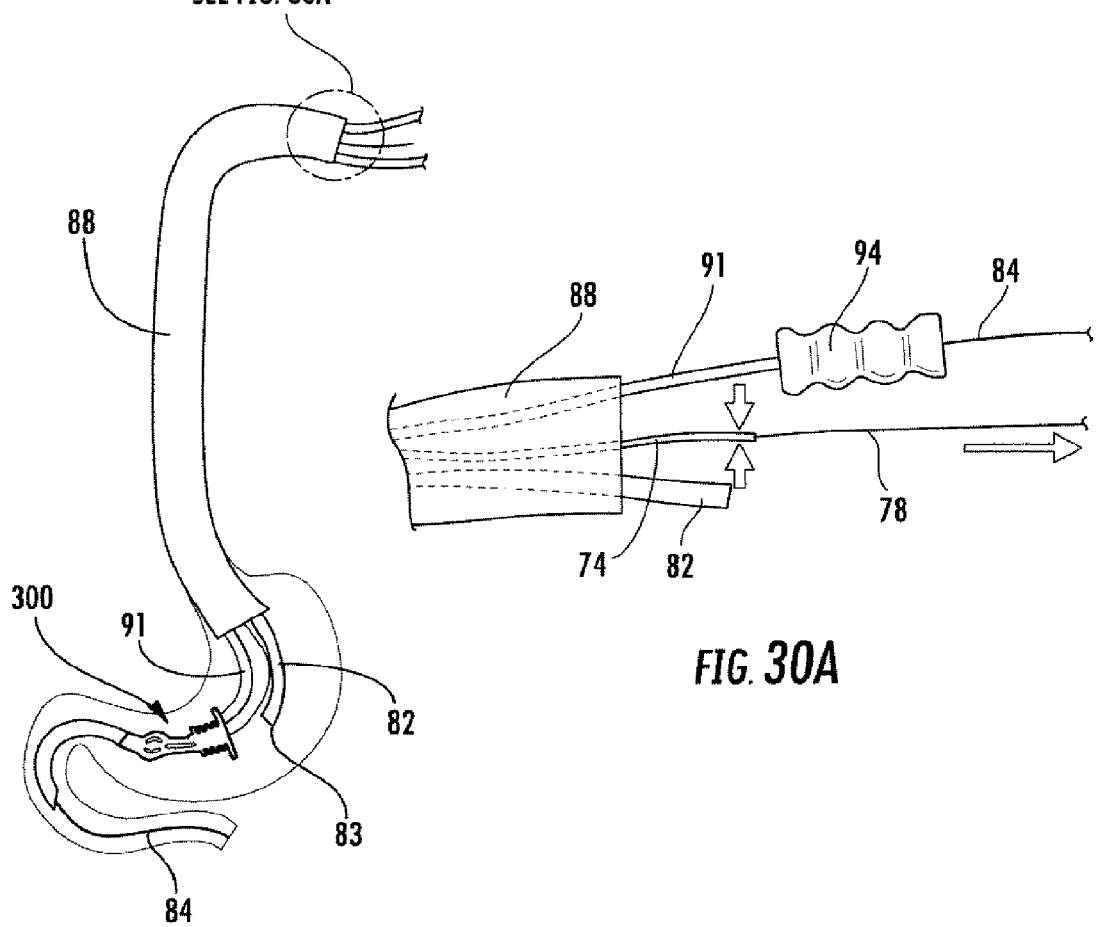
FIG. 30 is another step in the process of removing insertion equipment from the patient.
FIG. 30a is close-up view of the step shown in FIG. 30.
Figures 31, 31A:
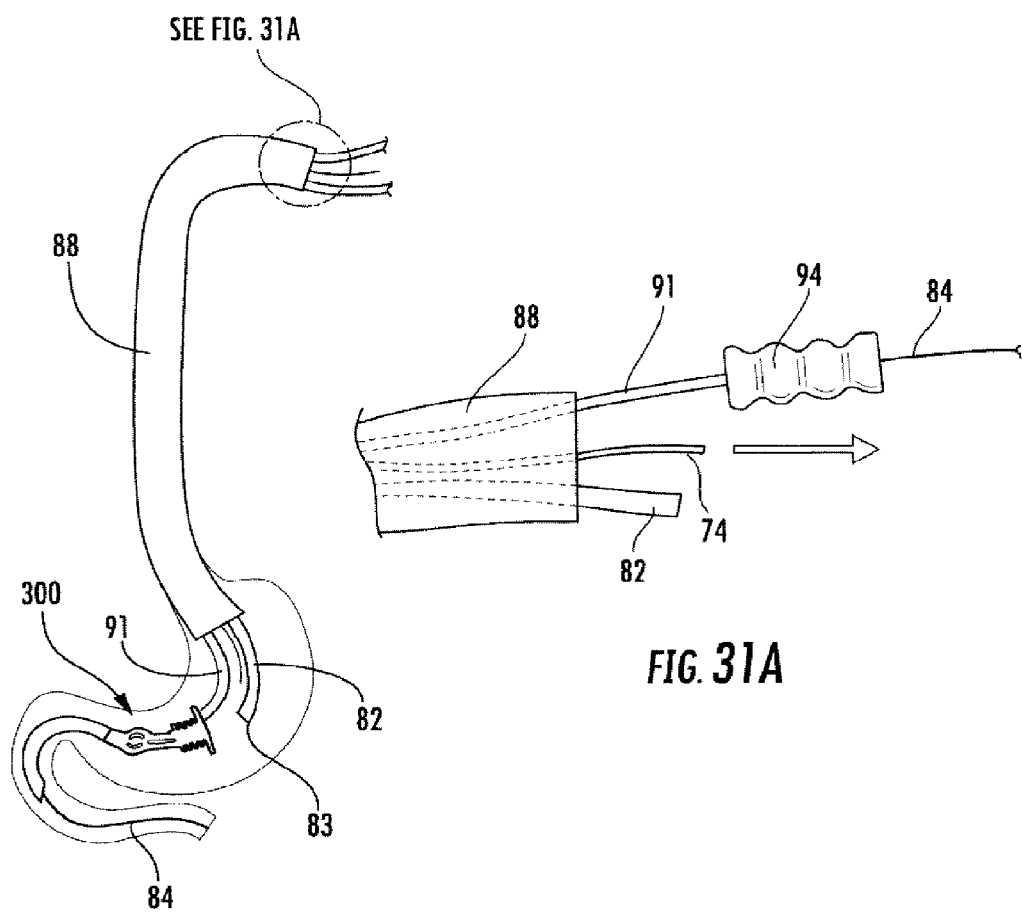
FIG. 31 is yet another step in the process of removing insertion equipment from the patient.
FIG. 31a is close-up view of the step shown in FIG. 31.
Figures 33, 33A:
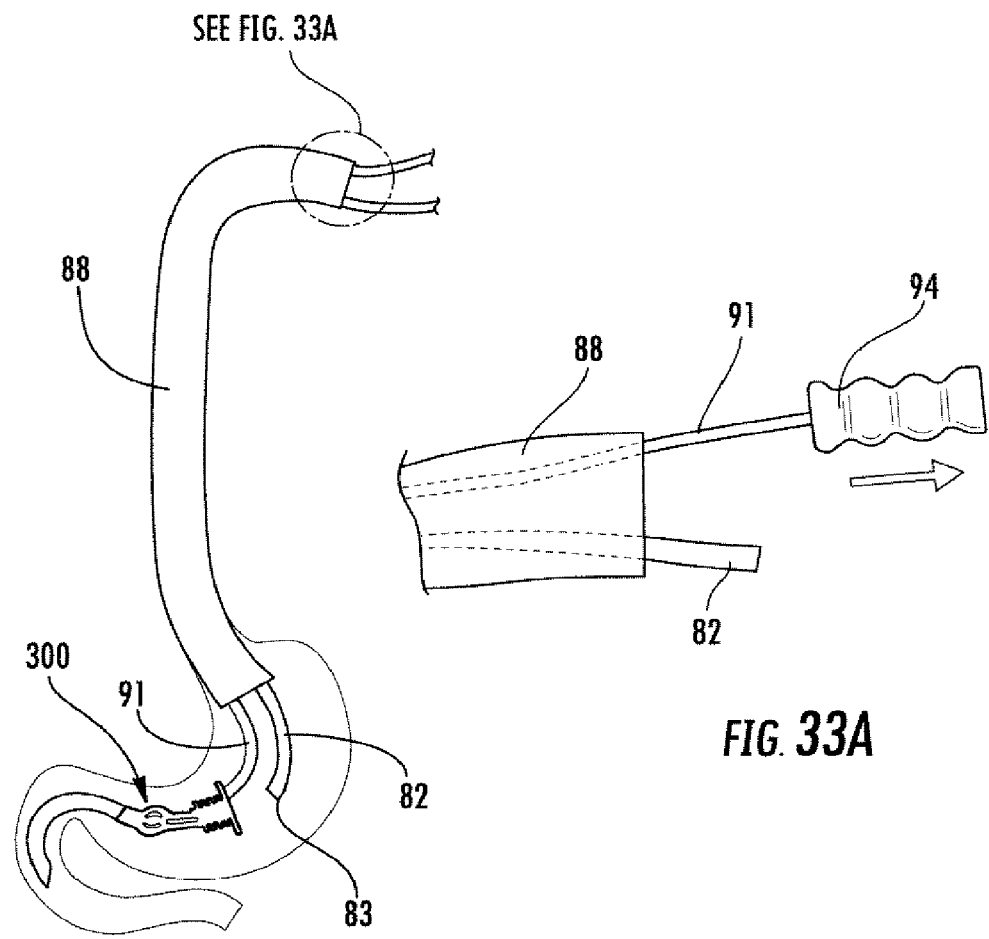
FIG. 33 is another step in the process of removing insertion equipment from the patient.
FIG. 33a is close-up view of the step shown in FIG. 33.
Figures 34, 34A:
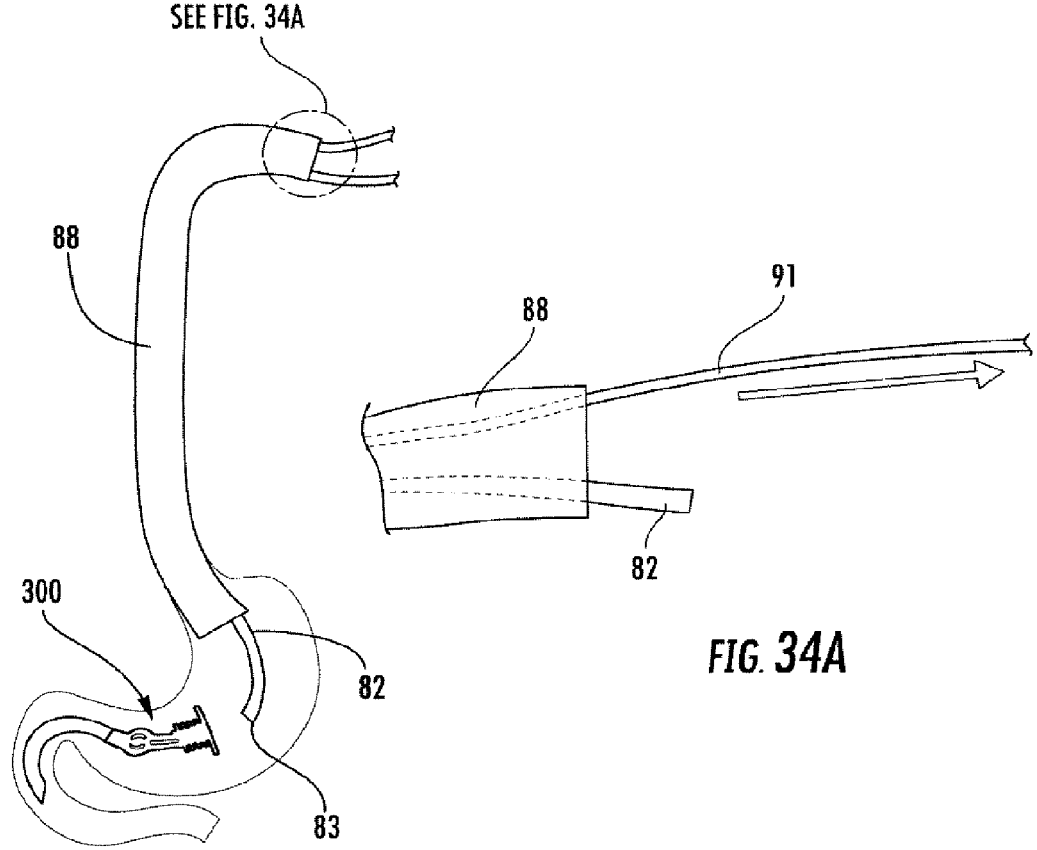
FIG. 34 is yet another step in the process of removing insertion equipment from the patient.
FIG. 34a is close-up view of the step shown in FIG. 34.
Figure 35:
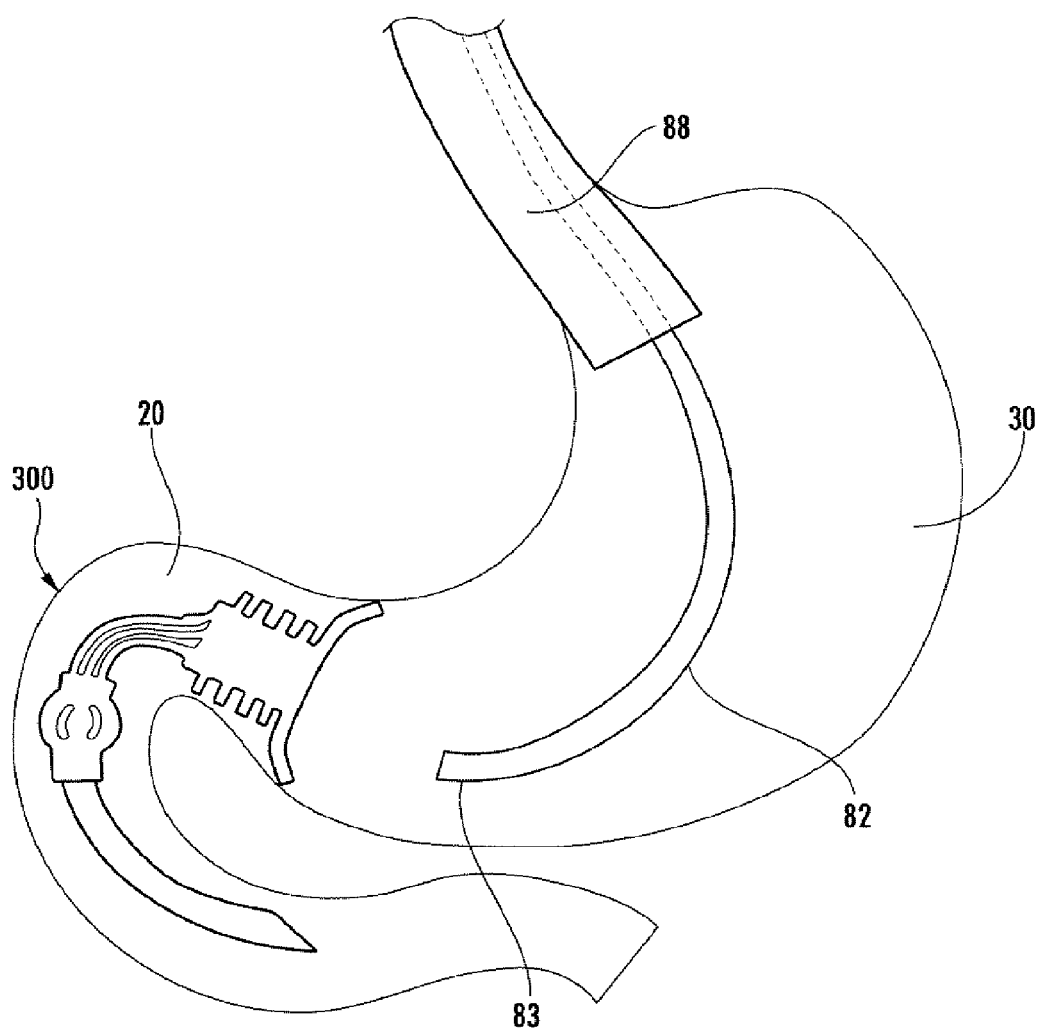
FIG. 35 is the insertion of the gastroscope to check the proper positioning of the implant shown in FIG. 21.

As shown in FIG. 25, implant 300 is inserted through esophagus 92 and into stomach 30 by pushing proximal end 97 of medium tube 91, which preferably includes medium tube handle 73. When implant 300 is disposed within the patient, medium tube 91 translates the insertion force applied by the surgeon. Because medium tube 91 is not able to pass through passage 339, distal pressure applied to medium tube 91 thusly translates into movement of implant 300. It should be understood that medium tube 91 should be flexible, yet rigid enough that a force applied to a proximal end 97 thereof may be effectively translated to distal end 95 thereof without buckling medium tube 91. Although medium tube handle 73 is available for manipulation, the surgeon may choose to additionally grasp medium tube 91 at a varying position along its length that is close to patient's mouth 70 during insertion.

Due to the length of implant 300, it is likely that at least part of sleeve 302 will be passed through pyloric sphincter 20 prior to the entirety of implant 300 being disposed within stomach 30. Further, because of the size of implant 300, gastroscope 82 may be reinserted into stomach 30 after implant 300 is inserted. During insertion, it should be ensured that any of the above-mentioned sutures do not become tangled, and that the proximal-most portion of gripping suture 78 end does not pass distally through mouth 70.

Over-tube 88 is preferably lubricated and inserted into the patient's mouth 70 and down esophagus 92 while being slid over small tube 86, medium tube 91, gastroscope 82, and any additional sutures and/or implantation tools. It is conceivable that over-tube 88 be inserted prior to the insertion of implant 300, though such may require implant 300 to be differently configured to fit within over-tube 88, which is narrower than esophagus 92. Preferably, over-tube 88 is inserted to protect esophagus 92, GE junction 35, and other internal bodily tissue from scarring when the various tubes and sutures are used during implantation, actuation, and removal of implant 300.

With implant 300 inserted such that pyloric columns 308 are adjacent pyloric sphincter 20 and top portion 306 is in its inverted position, distal end 81 of over-tube 88 is positioned in stomach 30 adjacent top portion 306. Because manipulation of top portion 306 into its nested position fortifies and substantially anchors implant 300 with respect to the surrounding tissue, it is preferable that implant 300 be placed as close to its final contracted position as possible prior to such manipulation.

As shown in FIGS. 3 and 27-28a, pulley system 72 is actuated through over-tube 88 to manipulate top portion 306 into its nested position. Grip 76 is pulled in a proximal direction, thusly pulling gripping suture 78 and bead suture 71 by way of loop 66. As loop 66 and second end 68 of bead suture 71 are pulled proximally, bead 79 is forced distally along send end 68 of bead suture 71, contacts narrow portion 312 of top portion 306, and forces top portion 306 into its nested position. Throughout this process, small tube 86 and/or medium tube 91 may be held in position to prevent implant 300 from moving proximally when grip 76 is pulled.

After top portion 306 is in its nesting position, gripping suture 78 may be disengaged from implant 300. Sheath may be moved slightly in a distal direction with respect to gripping suture 78 in order to expose gripping suture knot 69, as shown in FIGS. 27 and 27a. Either first end 75 or second end 77 of gripping suture 78 is cut at a point distal of gripping suture knot 69. Grip 76 is then pulled proximally, which pulls the uncut end of gripping suture 78 while the other end thereof travels distally through sheath 74 and loop 66 of bead suture 71, and passes proximally from the patient. Sheath 74 may be removed either during or after removal of gripping suture 78. Over-tube 88 may then be removed, or may alternatively be left in the patient during the subsequent checking of implant 300.

Figure 36:
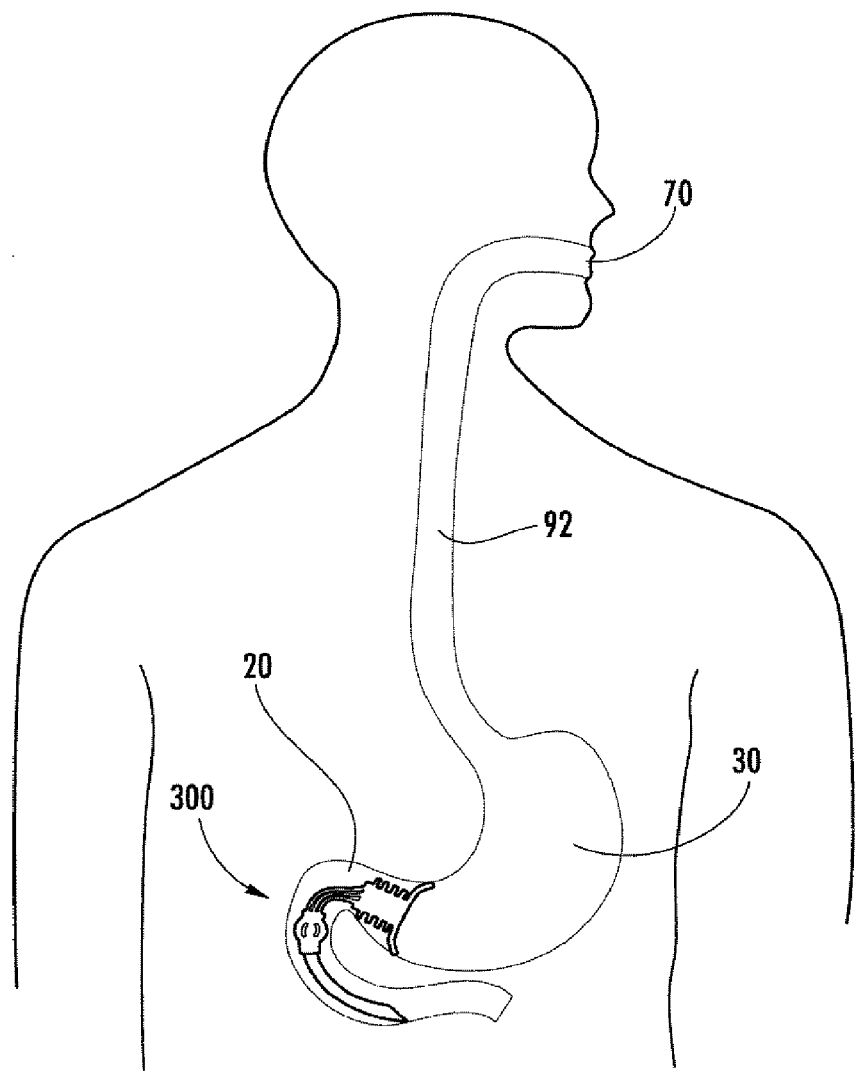
FIG. 36 is the implant shown in FIG. 21 located adjacent the pyloric sphincter.

Although implant 300 should now be substantially in its final position, with pyloric columns 308 disposed within pyloric sphincter 20, medium tube 91 may be used to further appropriately position implant 300. Gastroscope 82 and/or fluoroscope 96 may be used to confirm the final placement of implant 300. With implant 300 in its deployed state, guidewire 84, small tube 86, medium tube 91, and any other instrument or device may be gently pulled and removed from the patient. After all tools and devices have been removed, gastroscope 82 and/or fluoroscope 96 may be used to inspect implant 300 to confirm correct assembly and location as shown in FIG. 36. Gastroscope 82, fluoroscope 96, and over-tube 88 may then be removed.

Figure 37:
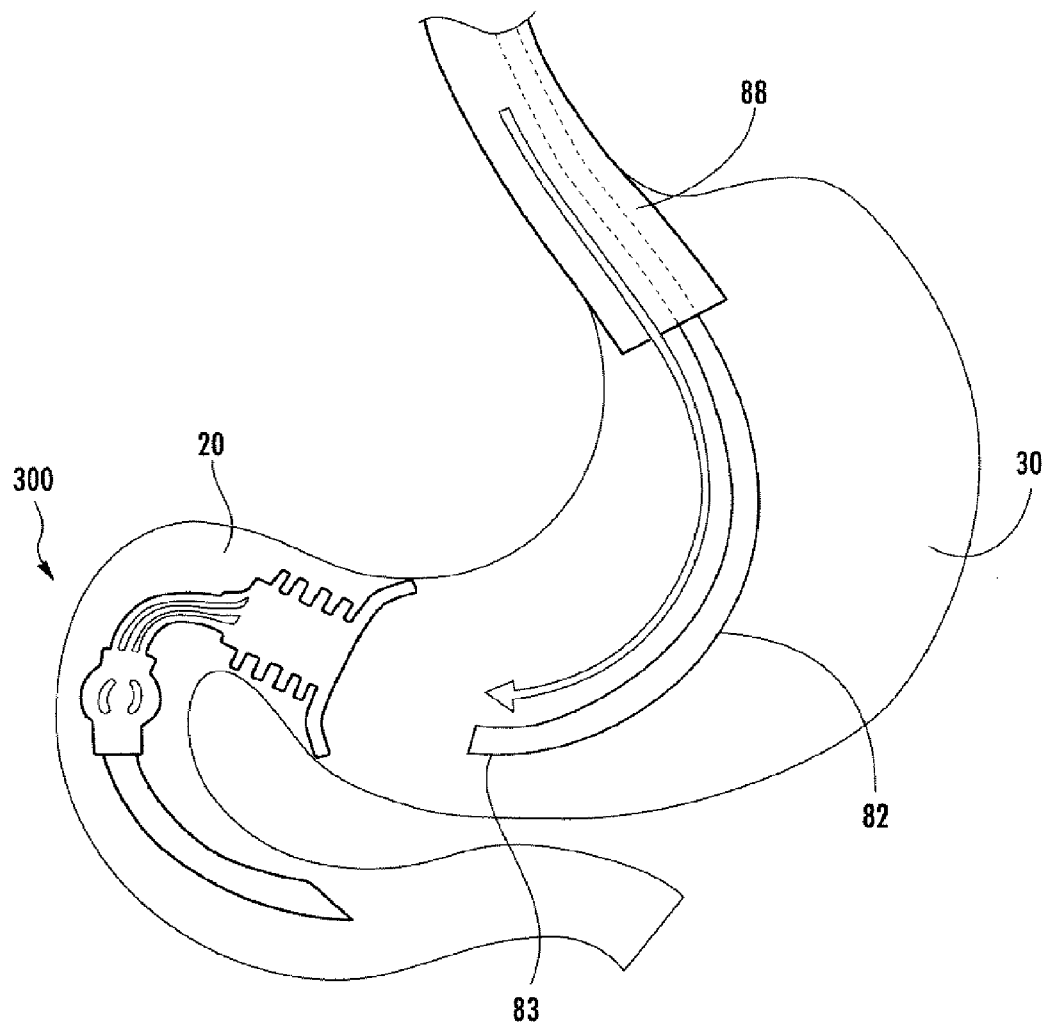
FIG. 37 is a step in the process of removing the implant shown in FIG. 21 from the patient.
Figure 38:
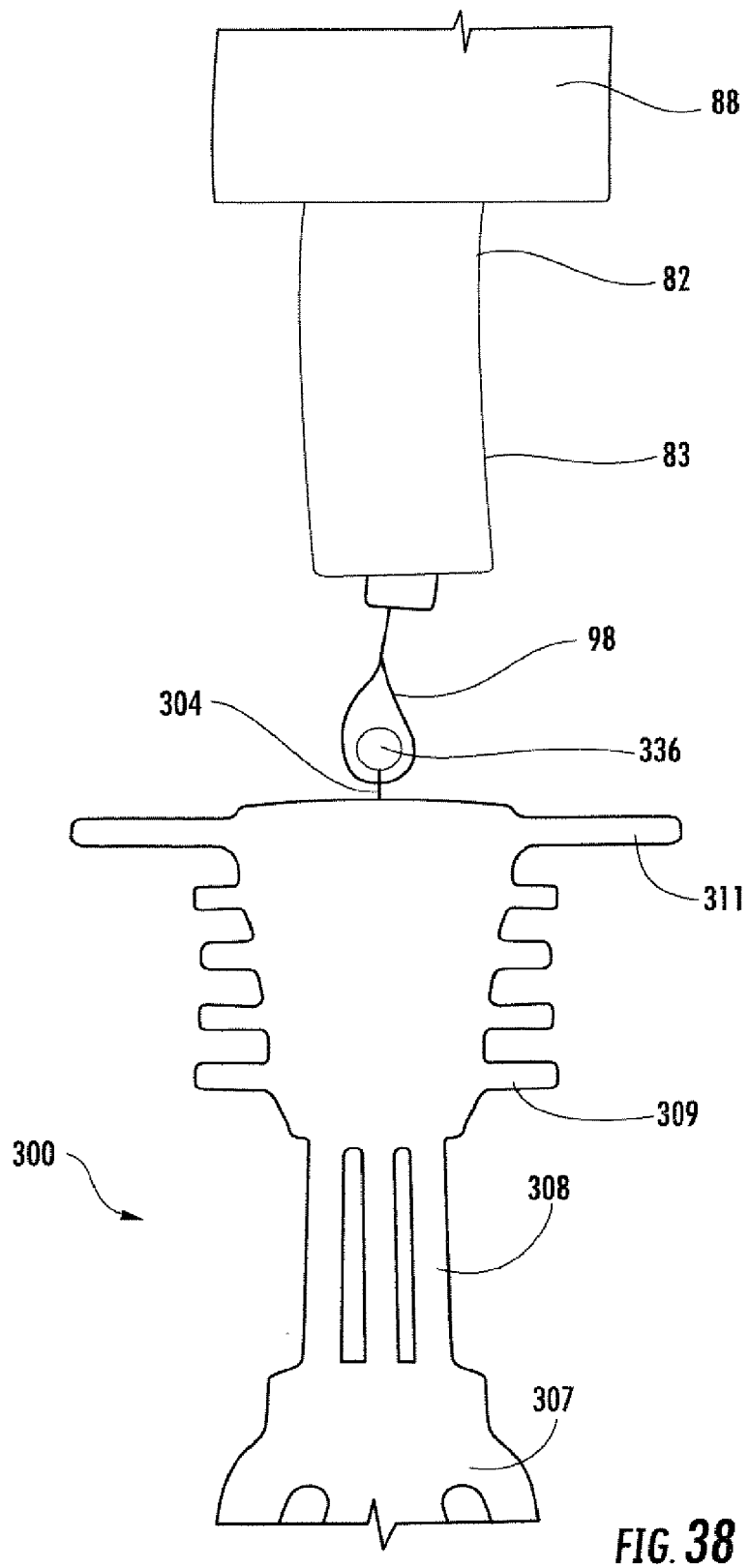
FIG. 38 is the process of actuating the implant shown in FIG. 21 from a nested position to an inverted position.
Figure 39:
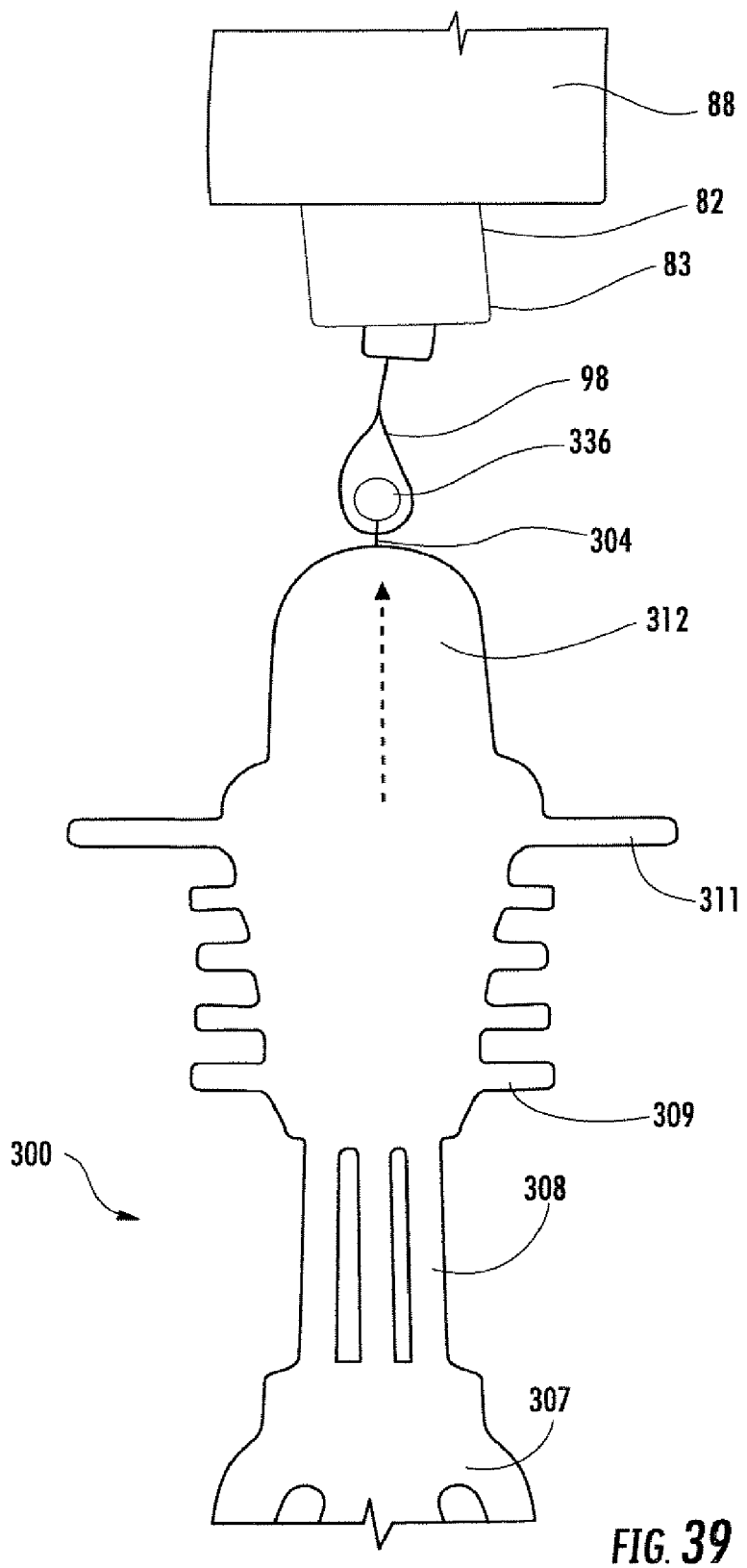
FIG. 39 is the implant shown in FIG. 21 actuated into its inverted position.
Figure 40:
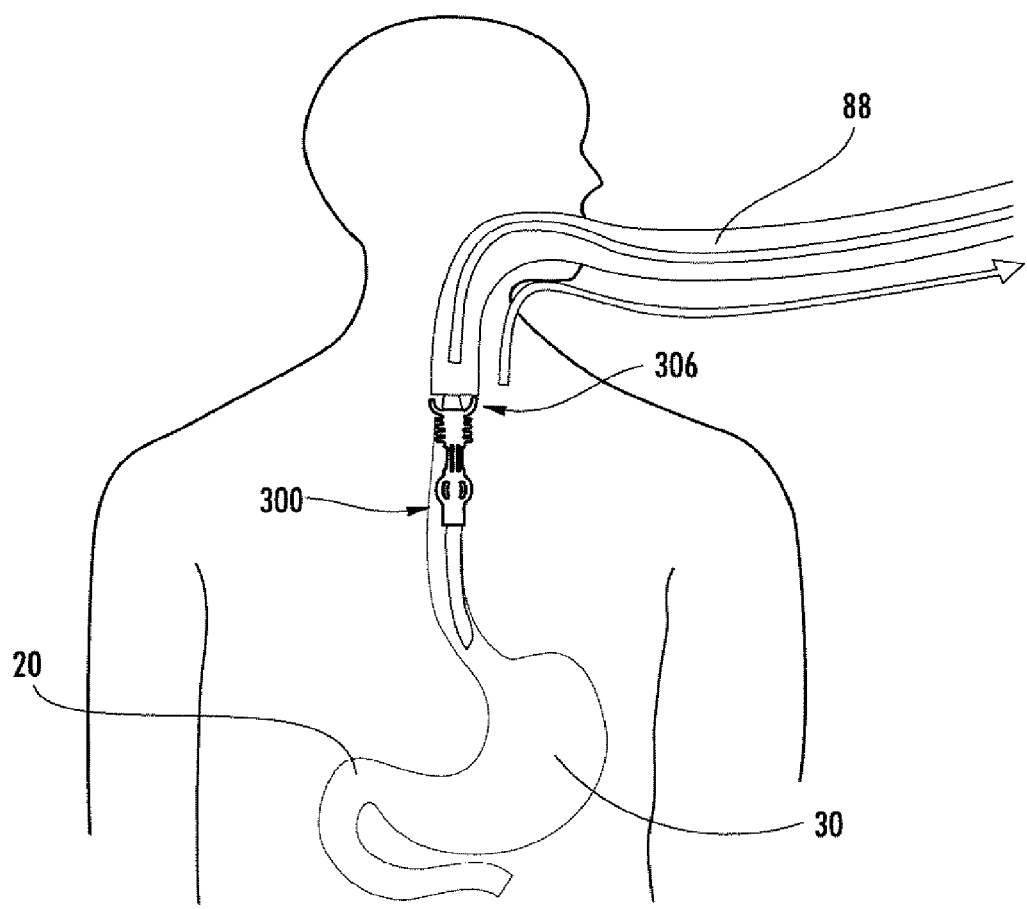
FIG. 40 is the removal of the implant shown in FIG. 21 from the patient's esophagus.

The following describes a method of removing a "top hat" style implant. Over-tube 88 is preferably lubricated and inserted through esophagus 92 into stomach 30. Gastroscope 82 is preferably lubricated, inserted through over-tube 88, and preferably positioned such that its distal end 83 is adjacent to top portion 306, as shown in FIG. 37. Snare 98 is inserted through gastroscope 82 and oriented around proximal anchor 336 of actuation suture 304. Although snare 98 is preferred, forceps 93 (not shown), grasper 99 (not shown), or any other similar device may be used for removal of implant 300. Snare 98 is pulled proximally, thereby pulling actuation suture 304 and forcing distal anchor 337 against narrow portion 312 of top portion 306. Top portion 306 is thusly manipulated into its inverted position. If during this inversion process, top portion 306 does not invert, but rather implant 300 moves proximally out of pyloric sphincter 20, implant 300 should continue to be pulled until it is disposed in the GE junction 35. The GE junction 35 should provide sufficient resistance to allow for inversion of top portion 306. Once top portion 306 is in its inverted position, gastroscope 82, over-tube 88, and snare 98 (which maintains its connection with implant 300 via actuation suture 304) are preferably pulled from the patient all at once.

Figure 7:
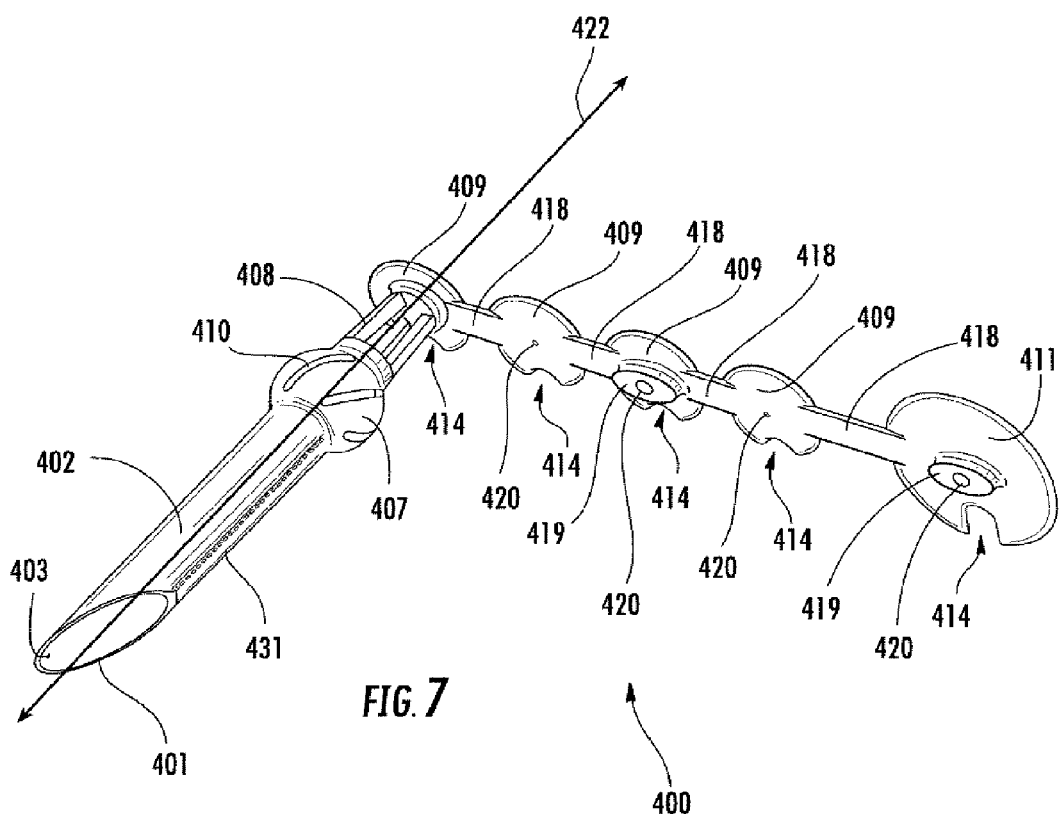
FIG. 7 is a perspective view of an "accordion" style implant according to another embodiment of the present invention.
Figure 9:
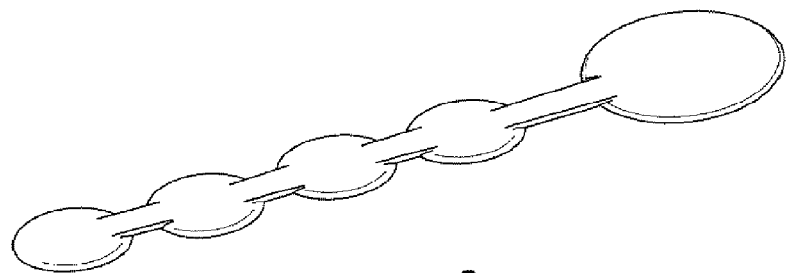
FIGS. 8 and 9 are perspective views of the flanges of the implant shown in FIG. 7 in a contracted position and a resting position, respectively.
Figure 8:
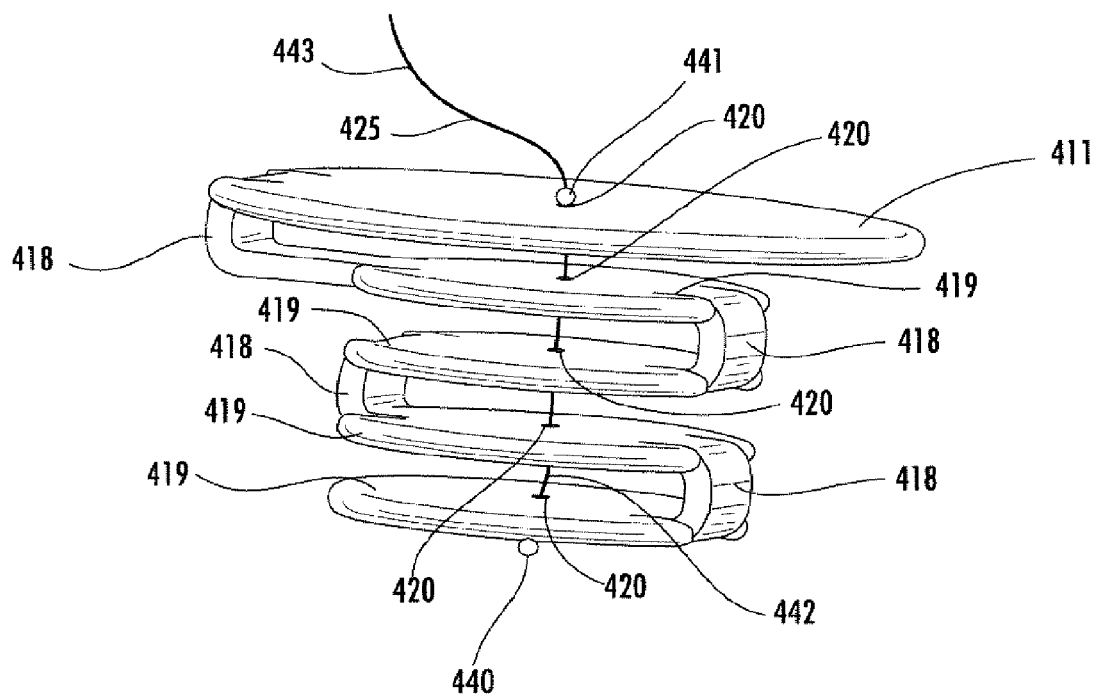
Figure 10:
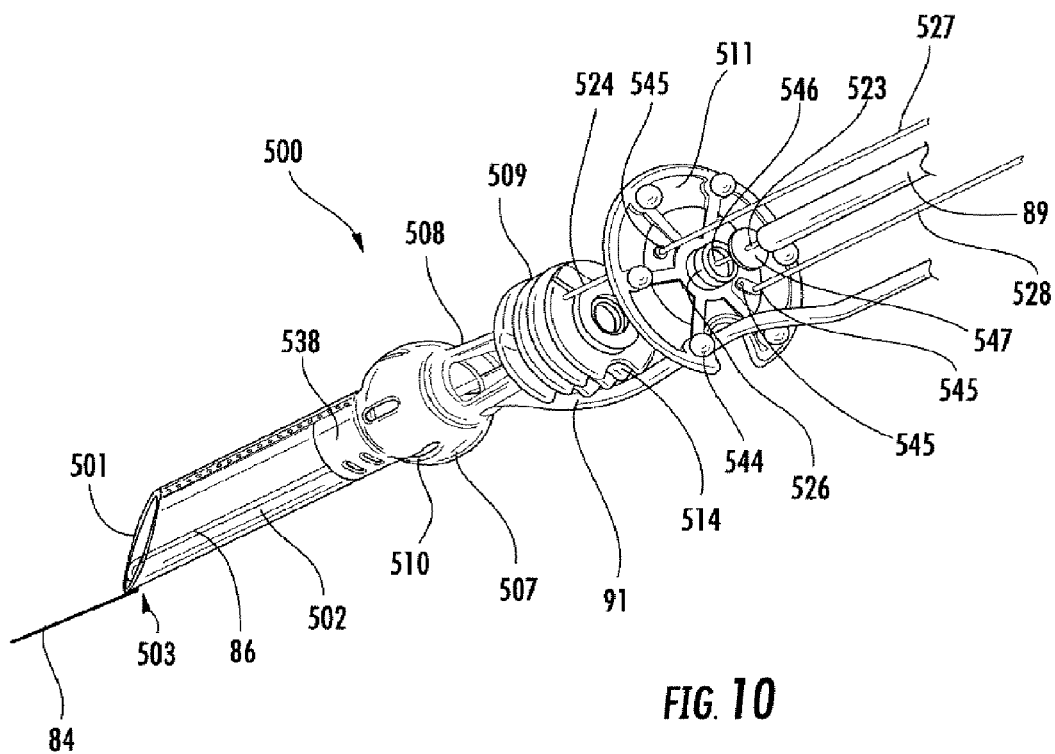
FIG. 10 is a perspective view of a "spiral" style implant according to another embodiment of the present invention.
Figure 11:
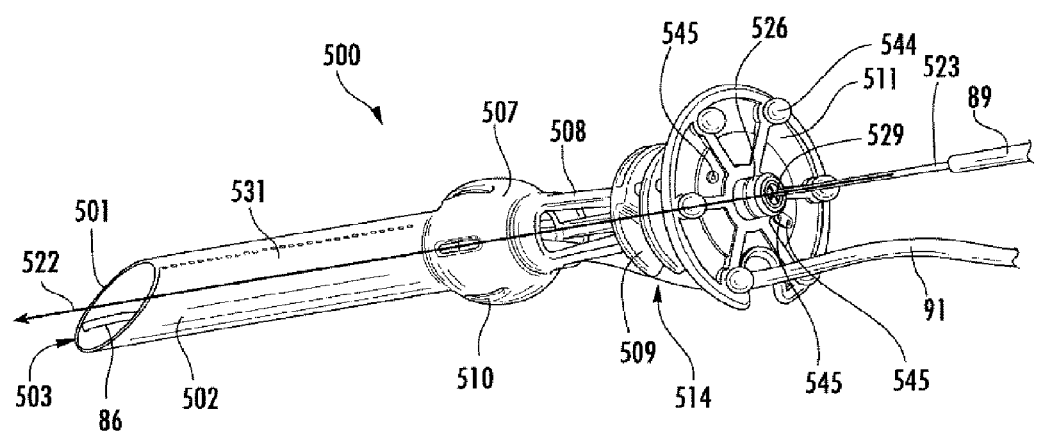
FIG. 11 is another perspective view of the implant shown in FIG. 10.

The following is a description of an "accordion" style implant. FIGS. 7-9 depict implant 400, which is one embodiment of an "accordion" style implant. Implant 400 includes many similarities to the aforementioned "top hat" style implant, and like elements will be referenced by like numerals. Implant 400 includes a sleeve 402, a duodenal sphere 407, at least one pyloric column 408, and at least one disc-shaped flange 409. Each flange 409 is connected to each adjacent flange 409 through a connector 418, such that the plurality of flanges 409 is connected in series. Each flange 409 preferably includes an outer circumference with a recess 414 therein. Connectors 418 are preferably comprised of the same material as the rest of implant 400, and thus are able to flex and bend. However, connectors 418 may also be comprised of a different material and grafted onto flanges 409.

Each flange 409 preferably includes one mound 419 and one hole 420. As shown in FIGS. 7 and 9 when implant 400 is in a resting position, a mound 419 is disposed on alternating proximal and distal sides of successive flanges 409. Flange 409 located closest to pyloric columns 408 may not include a mound 419. Each mound 419 provides for spacing between adjacent flanges 409 when implant 400 is in a contracted position, wherein the axis of each hole 420 is aligned. The contracted position of implant 400 can be achieved by manipulating flanges 409 such that implant 400 closely resembles the configuration of implant 100 wherein the plurality of disc-shaped flanges 409 is disposed in a stacked configuration, as shown in FIG. 8. In its resting position, disc-shaped flanges 409 are disposed in a linear configuration, as shown in FIGS. 7 and 9. Of course, one difference between implant 100 and implant 400 is that flanges 109 of implant 100 are connected by one or more struts 105, whereas flanges 409 of implant 400 are connected by one or more connectors 418. The result is that implant 400 in its contracted position, from a proximal-to-distal direction, will have in succession inlet 411, mound 419, flange 409, mound 419, flange 409, mound 419, and so on until the distal-most flange 409 connects to pyloric columns 408. It is noted that certain elements, such as mounds 419 and recesses 414, are omitted from FIGS. 8 and 9 in order to more clearly depict the respective contracted and resting positions of implant 400.

The following describes a method of inserting an "accordion" style implant. The steps of the above-described method with respect to the "top hat" style implant are incorporated herein to the present method. Of course, certain aspects of the following method may differ as the variations between the different embodiments of the implants are taken into account. Implant 400 enters and exits the patient in its resting position through esophagus 92, and is ultimately positioned in its operative state, wherein the at least one pyloric column 408 is adjacent to pyloric sphincter 20.

Initially, gastroscope 82 is lubricated, inserted into patient's mouth 70, and fed through esophagus 92 and GE junction 35 into stomach 30. Gastroscope 82 should ultimately be positioned such that its distal end is adjacent to pyloric sphincter 20. Preferably, the hydrophilic coating of guidewire 84 is hydrated and inserted through gastroscope 82. Guidewire 84 is passed through pyloric sphincter 20, which may be aided by manipulation of gastroscope 82. It may also be beneficial to pass distal end 83 of gastroscope 82 through pyloric sphincter 20 in order to maneuver guidewire 84 through same. There should preferably be at least about 30-40 centimeters of the length of guidewire 84 passed distally through pyloric sphincter 20 and into small intestine 40 so that any further movement of guidewire 84 during the insertion procedure does not result in the accidental removal of the distal end of guidewire 84 to a position proximal of pyloric sphincter 20. Of course, the length of guidewire 84 that should preferably be passed distally through pyloric sphincter 20 will vary according to different patients and/or procedures and may be less or more than 30-40 centimeters. After guidewire 84 is appropriately positioned, gastroscope 82 is removed from the patient. Fluoroscope 96 may then be used to check the positioning of guidewire 84.

As mentioned above, implant 400 should be preassembled with any necessary implantation tools and instruments, of course taking into account any differences in structure between the "top hat" and "accordion" styles of implants. Implant 400, while in its resting position, is thoroughly lubricated. Implant 400, small tube 86, and medium tube 91 are moved distally along guidewire 84 until implant 400 is positioned to be advanced down esophagus 92. Again, it is noted that during this procedure care must be taken not to pull guidewire 84 proximally out of small intestine 40.

Implant 400 is inserted through esophagus 92 and into stomach 30 by pushing proximal end 97 of medium tube 91, which preferably includes medium tube handle 73. During insertion, flanges 409 trail the rest of implant 400. Hole 403 of implant 400 is smaller than the outer diameter of small tube 86. Because medium tube 91 is not able to pass through passage 439, distal pressure applied to medium tube 91 thusly translates into movement of implant 400. It should be understood that medium tube 91 should be flexible, yet rigid enough that a force applied to proximal end 97 thereof may be effectively translated to distal end 95 thereof without buckling medium tube 91. Although medium tube handle 73 is available for manipulation, the surgeon may choose to additionally grasp medium tube 91 at a varying position along its length that is close to patient's mouth 70 during insertion.

The distal-most connector 418 may be bent to align flanges 409 with the direction of insertion. Due to the length of implant 400 and the extended flanges 409, it is likely that at least part of sleeve 402 will be passed through pyloric sphincter 20 prior to the entirety of implant 400 being disposed within stomach 30. Further, because of the size of implant 400, gastroscope 82 may be reinserted into stomach 30 after implant 400 is inserted. During insertion, it should be ensured that any of the above-mentioned sutures do not become tangled, and that the proximal-most portion of gripping suture 78 end does not pass distally through mouth 70.

With implant 400 inserted with flanges 409 in its resting position, over-tube 88 is preferably lubricated and inserted into the patient's mouth 70 and down esophagus 92 while being slid over small tube 86, medium tube 91, gastroscope 82, and any additional sutures and/or implantation tools. Distal end 81 of over-tube 88 should preferably be positioned in stomach 30 adjacent to the proximal-most flange 409.

An accordion suture 425, shown in FIG. 8, is disposed through hole 420 on each flange 409, and includes a first end 442 and a second end 443. A first accordion bead 440 is attached to first end 442. Second end 443 extends proximally from implant 400, while a second accordion bead 441 is secured to accordion suture 425 between first end 442 and second end 443. First accordion bead 440 is positioned distally of the distal-most flange 409 and has a diameter such that it may not pass proximally through hole 420 of the distal-most flange 409. Prior to insertion, second accordion bead 441 is disposed proximally of the distal-most flange 409 and distally of the next proximal flange 409. Second accordion bead 441 has a diameter that is slightly larger than the diameter of hole 420. The yielding nature of implant 400 will thusly allow for the passage of second accordion bead 441 through each hole 420 when a minimal force is applied.

Accordion suture 425 is preassembled as threaded through each successive hole 420 or aperture of each successive flange 409. To move implant 400 into its contracted position, the surgeon preferably braces implant 400 from proximal movement by holding medium tube 91. Accordion suture 425 is preferably held from a position proximal of implant 400 so that it remains substantially taut. The surgeon then preferably pushes on the proximal-most flange 409 with a tube or pushing device (not shown). Such a tube or pushing device may be a suture sheath 89, as depicted and described more clearly below. The purpose of the tube or pushing device is to force flanges 409 distally such that they slide along accordion suture 425. The tube or pushing device need not be adapted to be disposed about accordion suture 425. As flanges 409 are pushed distally, second accordion bead 441 passes through each successive hole 420 of flanges 409 until flanges 409 are disposed in the contracted position, as shown in FIG. 8. Preferably, while flanges 409 are in the contracted position, first accordion bead 440 is disposed to be in contact with the distal side of the distal-most flange 409, while second accordion bead 441 is disposed to be in contact with the proximal side of the proximal-most flange 409. As second accordion bead 441 passes through each hole 420, the surgeon will encounter a tactile feel as second accordion bead 441 "pops" through each hole 420. Implant 400 will remain in its contracted position after the proximal force is released from accordion suture 425, which remains substantially taut and essentially maintains flanges 409 in the contracted position. Implant 400 is now in its fully assembled state. Gastroscope 82 and/or fluoroscope 96 may be used to inspect implant 400 to confirm that such is correctly assembled. Over-tube 88 may then be removed.

Although implant 400 should now be substantially in its final position, with pyloric columns 408 disposed within pyloric sphincter 20, medium tube 91 may be used to further appropriately position implant 400. Gastroscope 82 and/or fluoroscope 96 may be used to confirm the final placement of implant 400. With implant 400 in its deployed state, guidewire 84, small tube 86, medium tube 91, and any other instrument or device may be gently pulled and removed from the patient. After all tools and devices have been removed, gastroscope 82 and/or fluoroscope 96 may be used to inspect implant 400 and to confirm correct assembly and location. Gastroscope 82, fluoroscope 96, and over-tube 88 may then be removed.

The following describes a method of removing an "accordion" style implant. The steps of the above-described method with respect to the "top hat" style implant are incorporated herein to the present method. Of course, certain aspects of the following method may differ as the variations between the different embodiments of the implants are taken into account. Over-tube 88 is preferably lubricated and inserted through esophagus 92 into stomach 30. Gastroscope 82 is preferably lubricated, inserted through over-tube 88, and positioned such that its distal end 83 is adjacent to the proximal end of implant 400. Forceps 93 are inserted through gastroscope 82 and positioned adjacent the proximal-most flange 409. The proximal-most flange 409 should be pulled proximally by forceps 93, thereby forcing second accordion bead 441 distally through each hole 420 and returning flanges 409 to their resting position. If during the removal process second accordion bead 441 does not pass distally through any of holes 420, accordion suture 425 may be cut with scissors 90 at a point distal to second accordion bead 441 and removed. Once flanges 409 are in their resting position, gastroscope 82, over-tube 88, and forceps 93 (which maintain their connection with implant 400 via accordion suture 425) are preferably pulled from the patient all at once.

The following is a description of a "spiral" style implant. FIGS. 10-16 depict implant 500, which is one embodiment of a "spiral" style implant. Implant 500 includes many similarities to the aforementioned "top hat" and "accordion" style implants, and like elements will be referenced by like numerals. Implant 500 includes a sleeve 502, a duodenal sphere 507, at least one pyloric column 508, a helical or spiral flange 509, and a disc-shaped inlet 511. Inlet 511 preferably includes an outer circumference and a recess 514 disposed in the outer circumference. Implant 500 further includes a first suture 523 having a knot 529 and being attached to a bead 530, a second suture 524 having a fore end 527 and an aft end 528, and a plug 526. Plug 526 has the general external appearance of a nail, and includes a thru-hole 546. Disposed circumferentially about inlet 511 is a plurality of knobs 544. Of course, implant 500 could be manufactured with only one knob 544 and the position of same need not be adjacent to the perimeter of inlet 511.

Figure 12:
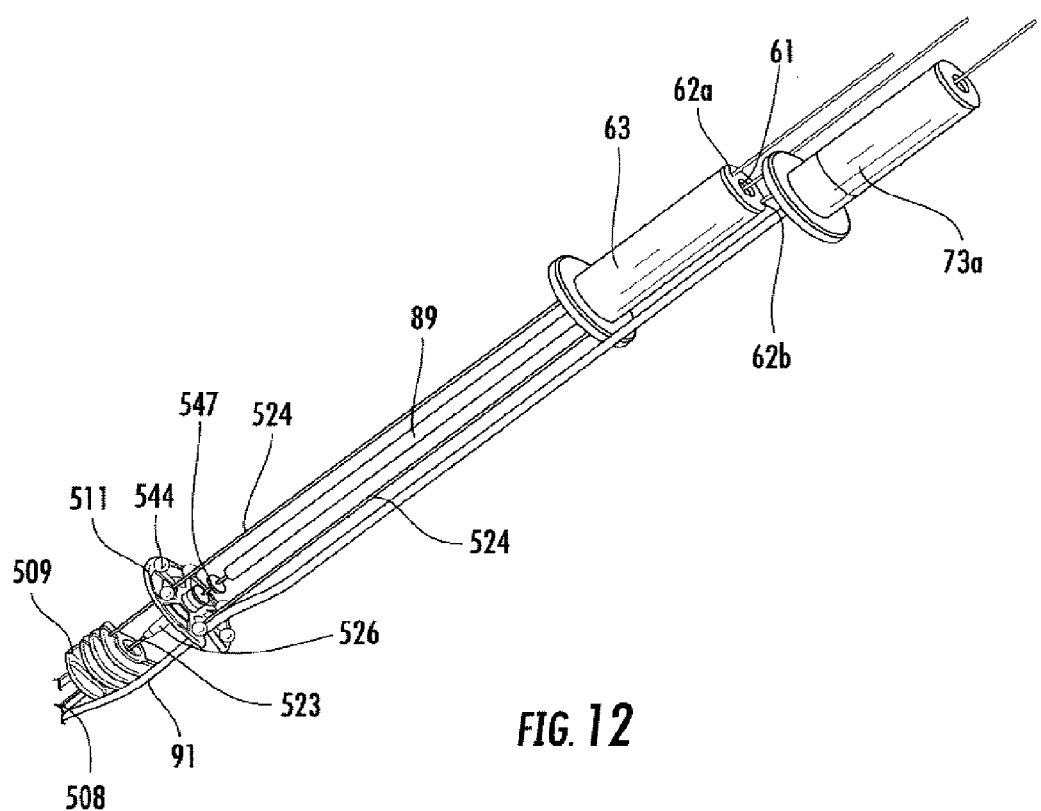
FIG. 12 is a perspective view of a proximal end of the implant shown in FIG. 10.
Figure 13:
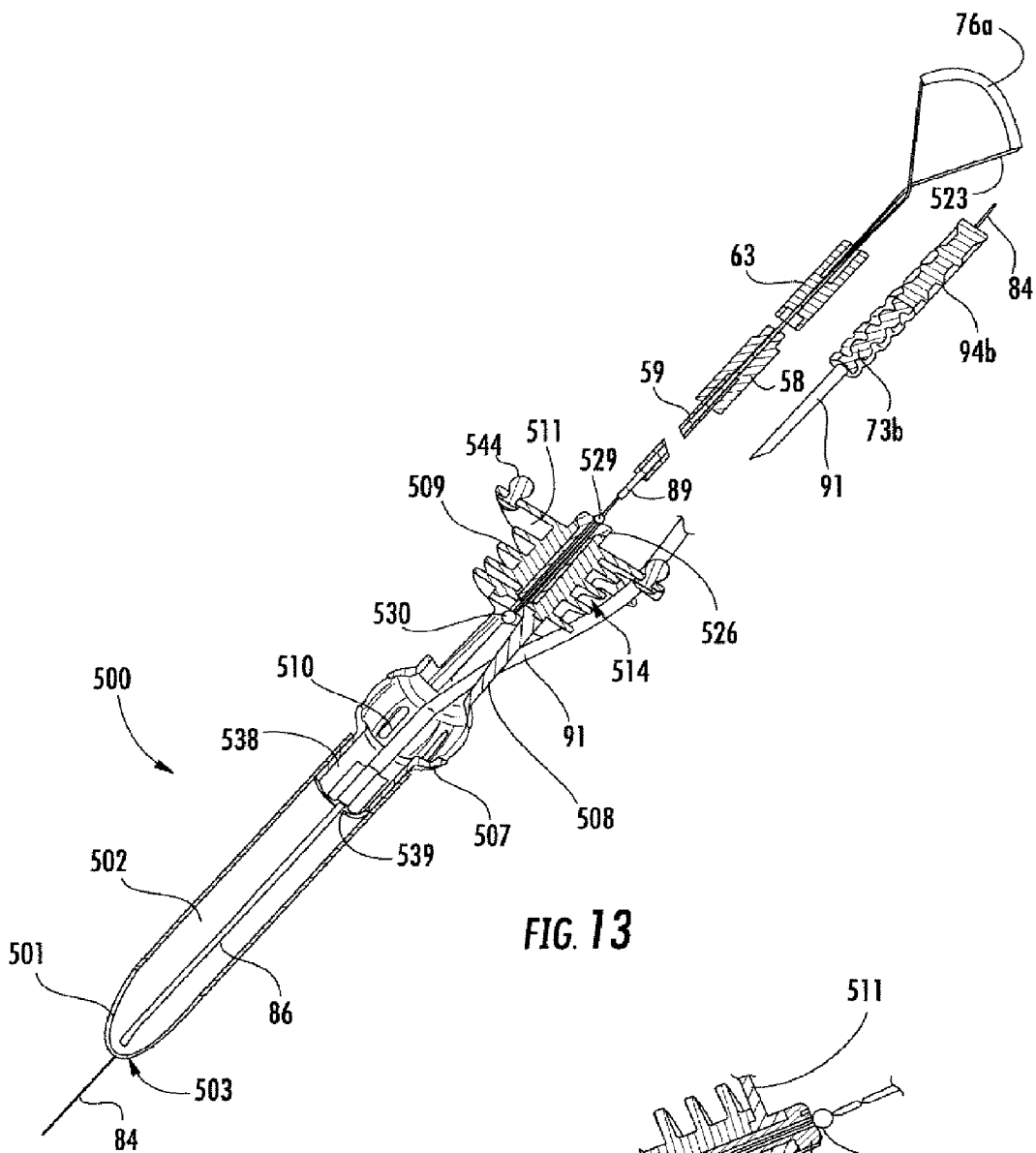
FIG. 13 is a sectional view of the implant shown in FIG. 10.
Figure 14:
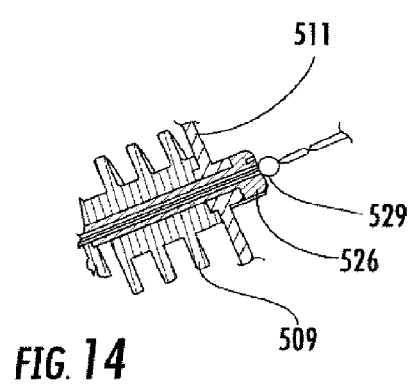
FIG. 14 is a close-up sectional view of the proximal end of the implant shown in FIG. 10.
Figure 15:
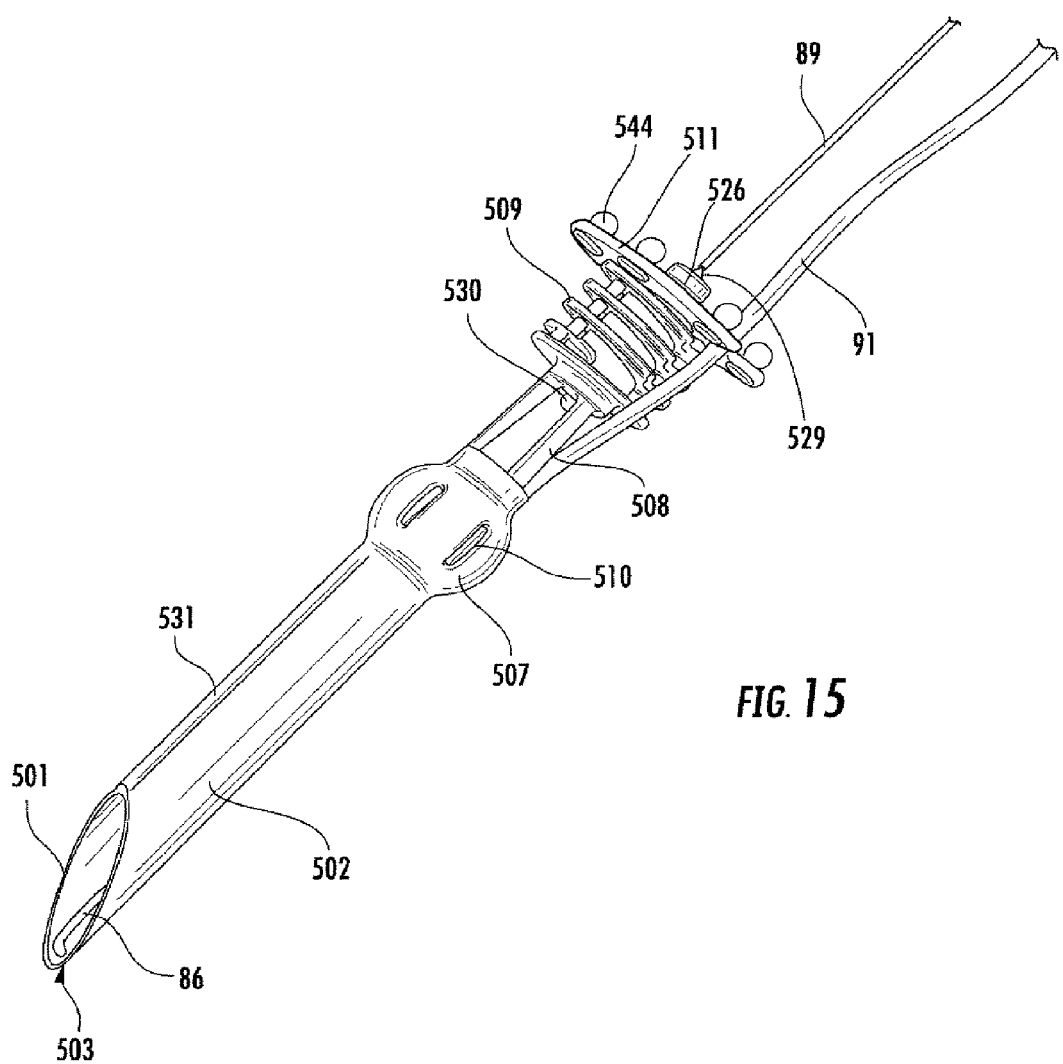
FIG. 15 is another perspective view of the implant shown in FIG. 10.
Figure 16:
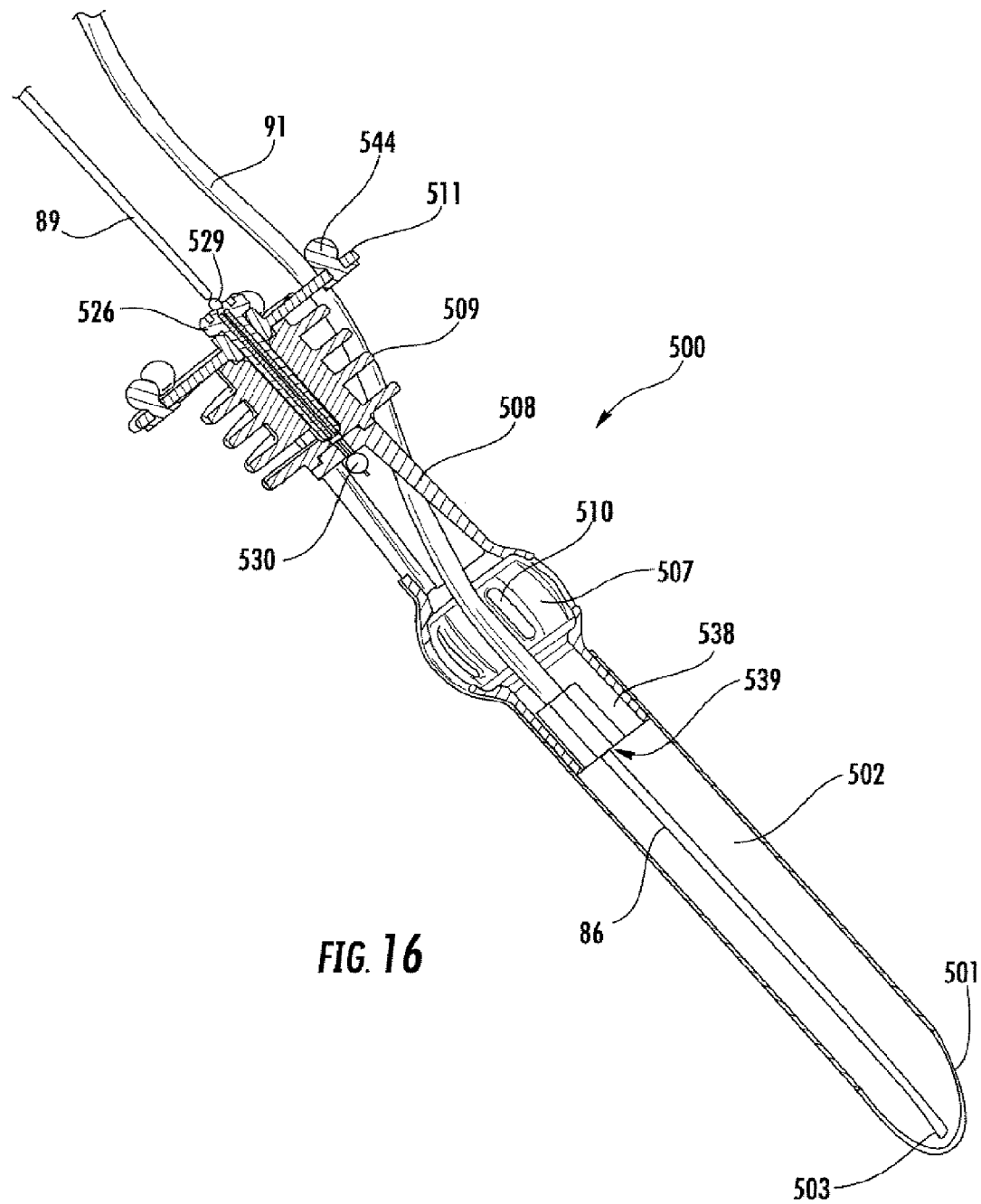
FIG. 16 is a sectional view of the implant shown in FIG. 10.
Figure 17:
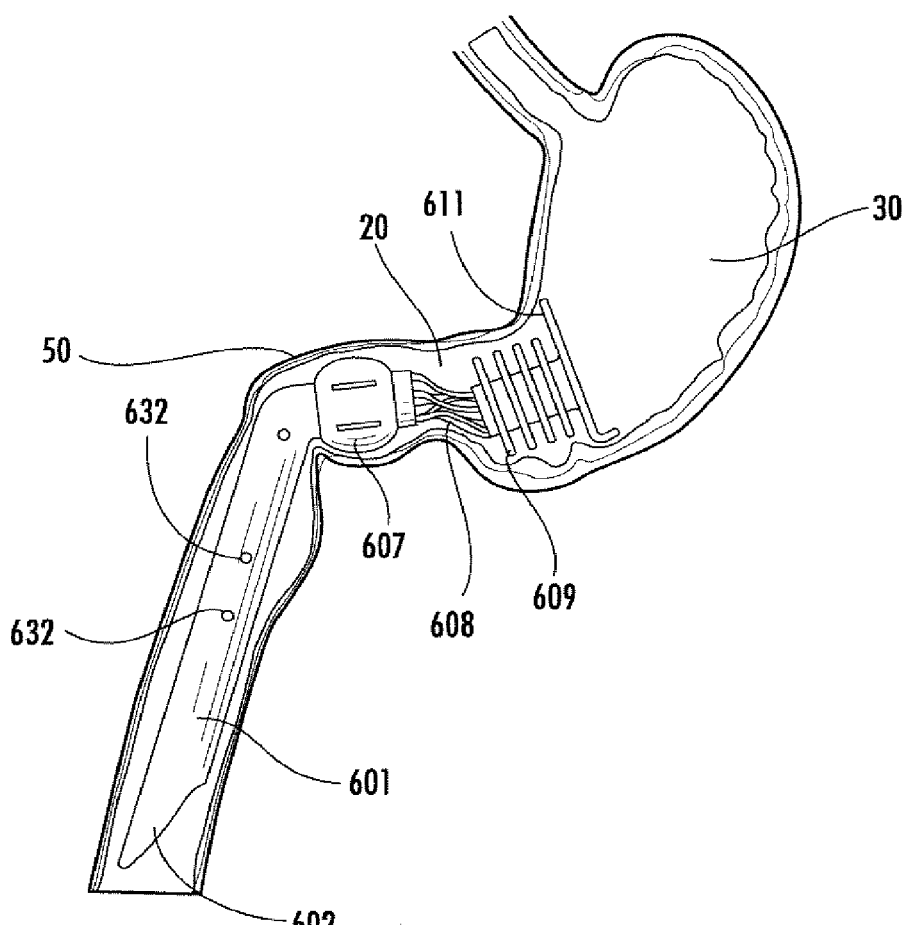
FIG. 17 is an implant of the present invention inserted in the GI tract of a patient.

Spiral flange 509 is a single unit that comprises a helically wound flange 509 extending along a longitudinal axis, and is similar in nature to the previously disclosed flanges 109, 209, 309, and 409. Due to the composition of spiral flange 509, it preferably includes a contracted position defining a contracted length and a contracted diameter and an extended position defining an extended length and an extended diameter. The extended length is longer than the contracted length and the extended diameter is smaller than the contracted diameter. The contracted position can be seen, for example, in FIG. 11. Further, one or more recesses 514 may be disposed in the outer edge of spiral flange 509. Recess 514 in inlet 511 and recesses 514 in the outer edge of spiral flange 509 may be axially aligned when spiral flange 509 is in the contracted position. A suture sheath 89 is provided and preferably includes a suture sheath handle 63, which has a central passage 61 for first suture 523 and side passages 62a, 62b for fore end 527 and aft end 528 of section suture 524 to extend proximally. A pusher tube 59 is also provided and preferably includes a pusher tube handle 58. Suture sheath 89 is preferably constructed to fit within pusher tube 59. Suture sheath handle 63 is connectable with pusher tube handle 58 to form a single unit. As shown in FIG. 12, medium tube 91 includes another embodiment of a medium tube handle 73a. Further shown in FIGS. 13 and 14, medium tube 91 includes another embodiment of a medium tube handle 73b and small tube 86 includes another embodiment of a small tube handle 94b. Disposed about the proximal most portion of first suture 523 is a grip 76a.

As mentioned above, implant 500 should be preassembled with any necessary implantation tools and instruments, of course taking into account any differences in structure between the "top hat," "accordion," and "spiral" styles of implants. As part of the preassembly, first suture 523 is preferably disposed through spiral flange 509 and thru-hole 546 of plug 526 such that bead 530 is disposed distally of both spiral flange 509 and plug 526. Knot 529 should preferably also be disposed distally of plug 526 but proximally of spiral flange 509 prior to insertion of implant 500. First suture 523 is preferably threaded proximally through a disc 547, suture sheath 89, and suture sheath handle 63. Second suture 524 passes through two or more inlet holes 545 of inlet 511 such that a fore end 527 and an aft end 528 of second suture 524 each extend proximally from implant 500. Pusher tube 59 is preferably disposed about suture sheath 89. Proximal of suture sheath handle 63, first suture 523 forms a loop, threads through grip 76a, and connects back to itself, preferably in a knot. It should be ensured that first suture 523 and second suture 524 do not become tangled.

The following describes a method of inserting a "spiral" style implant. The steps of the above-described methods with respect to the "top hat" style and "accordion" style implants are incorporated herein to the present method. Of course, certain aspects of the following method may differ as the variations between the different embodiments of the implants are taken into account. Implant 500 enters and exits the patient through esophagus 92 and is ultimately positioned in its operative state, wherein the at least one pyloric column 508 is adjacent to pyloric sphincter 20.

Initially, gastroscope 82 is lubricated, inserted into patient's mouth 70, and fed through esophagus 92 and GE junction 35 into stomach 30. Gastroscope 82 should ultimately be positioned such that its distal end is adjacent to pyloric sphincter 20. Preferably, a hydrophilic coating of guidewire 84 is hydrated and inserted through gastroscope 82. Guidewire 84 is passed through pyloric sphincter 20, which may be aided by manipulation of gastroscope 82. It may also be beneficial to pass a distal end 83 of gastroscope 82 through pyloric sphincter 20 in order to maneuver guidewire 84 through same. There should preferably be at least about 30-40 centimeters of the length of guidewire 84 passed distally through pyloric sphincter 20 and into small intestine 40 so that any further movement of guidewire 84 during the insertion procedure does not result in the accidental removal of the distal end of guidewire 84 to a position proximal of pyloric sphincter 20. Of course, the length of guidewire 84 that should preferably be passed distally through pyloric sphincter 20 will vary according to different patients and/or procedures and may be less or more than 30-40 centimeters. After guidewire 84 is appropriately positioned, gastroscope 82 is removed from the patient. Fluoroscope 96 may then be used to check the positioning of guidewire 84.

As mentioned above, implant 500 should be preassembled with any necessary implantation tools and instruments, of course taking into account any differences in structure between the "top hat," "accordion," and "spiral" styles of implants. Implant 500, small tube 86, and medium tube 91 are moved distally along guidewire 84 until implant 500 is positioned to be advanced down esophagus 92. Again, it is noted that during this procedure care must be taken not to pull guidewire 84 proximally out of small intestine 40.

Implant 500, with plug 526 disposed proximally of spiral flange 509, is thoroughly lubricated and moved distally along guidewire 84 until it is in a position to be advanced down esophagus 92. Again, it is noted that during this procedure care must be taken not to pull guidewire 84 out of small intestine 40. Implant 500 is inserted through esophagus 92 and into stomach 30 by pushing proximal end 97 of medium tube 91, which preferably includes medium tube handle 73. During insertion, spiral flange 509 may yield to the patient's tissue such that it expands into its expanded state. This allows for a narrower diameter of spiral flange 509 as it traverses esophagus 92. Implant 500 should also be advanced without inlet 511 and plug 526, although inlet 511 and plug 526 should preferably be connected with respective first suture 523 and second suture 524 at this point of the insertion procedure. Hole 503 of implant 500 is smaller than the outer diameter of small tube 86. Although medium tube handle 73 is available for manipulation, the surgeon may choose to additionally grasp medium tube 91 at a varying position along its length that is close to patient's mouth 70 during insertion.

Implant 500 is pushed through esophagus 92 and into stomach 30. Due to the length of implant 500, it is likely that at least part of sleeve 502 will be passed through pyloric sphincter 20 prior to the entirety of implant 500 being disposed within stomach 30. Further, because of the size of implant 500, gastroscope 82 may be reinserted into stomach 30 after implant 500 is inserted.

With implant 500 inserted with spiral flange 509 in its extended position, over-tube 88 is preferably lubricated and inserted into the patient's mouth 70 and down esophagus 92 while being slid over small tube 86, medium tube 91, gastroscope 82, and any additional sutures and/or implantation tools. Distal end 81 of over-tube 88 should preferably be positioned in stomach 30 adjacent to spiral flange 509.

It is conceivable that over-tube 88 be inserted prior to the insertion of implant 500, though such may require implant 500 to be differently configured to fit within a more narrow inner diameter of over-tube 88. Preferably, over-tube 88 is inserted to protect esophagus 92, GE junction 35, and other internal bodily tissue from scarring when the various tubes and sutures are used during implantation, actuation, and removal of implant 500.

Inlet 511 and plug 526 are advanced along respective first suture 523 and second suture 524 down esophagus 92 and into stomach 30 preferably by pushing distally on pusher tube handle 63. A small amount of tension in the proximal direction should be maintained with respect to first suture 523 and second suture 524 extending from patient's mouth 30 so that the same remain substantially taut through esophagus 92. After inlet 511 and plug 526 have been inserted into stomach 30, gastroscope 82 may be inserted into the stomach.

First suture 523 and fore end 527 and aft end 528 of second suture 524 are held while pusher tube 59 and suture sheath 89 are advanced toward implant 500. Resistance will notify the surgeon that plug 526 is in contact with knot 529. Pusher tube 59 is then pushed distally until knot 529 passes proximally through plug 526. As knot 529 is configured to pass through thru-hole 546 of plug 526 only under application of force, plug 526 is effectively secured to a location distal of knot 529. The distance between knot 529 and bead 530 on suture 523 should preferably be predetermined such that plug 526 engages spiral flange 509 and secures inlet 511 to same while forcing spiral flange 509 to maintain its contracted position.

Implant 500, in its operative state, should be substantially in its deployed position, with pyloric columns 508 disposed within pyloric sphincter 20. Medium tube 91 may be used to further appropriately position implant 500. Over-tube 88 may be removed, or may alternatively be left in patient during the subsequent checking of implant 500. Gastroscope 82 and/or fluoroscope 96 may be used to inspect implant 500 to confirm that such is correctly assembled and positioned.

Guidewire 84, small tube 86, medium tube 91, and any other instrument or device are gently pulled and removed from the patient. Scissors 90 may preferably be used to cut first suture 523 at a point proximal of knot 529, wherein the proximal portion of first suture 523 may then be removed. Second suture 524 is preferably removed by pulling either fore end 527 or aft end 528 in a proximal direction. Second suture 524 may alternatively be cut along its length, and both fore end 527 and aft end 528 pulled proximally. After all tools and devices have been removed, gastroscope 82 and/or fluoroscope 96 may preferably be used to inspect implant 400 and to confirm correct assembly and location Gastroscope 82, fluoroscope 96, and over-tube 88 may then be removed.

The following describes a method of removing a "spiral" style implant. The steps of the above-described method with respect to the "top hat" and "accordion" styles of implants are incorporated herein to the present method. Of course, certain aspects of the following method may differ as the variations between the different embodiments of the implants are taken into account. Over-tube 88 is lubricated and inserted through esophagus 92 into stomach 30. Gastroscope 82 is preferably lubricated, inserted through over-tube 88, positioned such that its distal end 83 is adjacent to the proximal end of implant 500. Snare 98 is inserted through gastroscope 82 and oriented over one of knobs 544 on inlet 511. Snare 98 is then pulled such that bead 530 advances proximally through spiral flange 509. It is noted that bead 530 is preferably configured so as not to pass through spiral flange 509 unless under a force applied by a surgeon. Thus, inlet 511, plug 526, and first suture 523 remain substantially connected during removal. Gastroscope 82 is removed with snare 98 such that the connection between inlet 511 and plug 526 are monitored during removal. Gastroscope 82 is reinserted with snare 98, which is used to grasp any portion of implant 500 to aid in removal of same. Of course, without plug 526 forcing spiral flange 509 into its contracted position, spiral flange 509 is preferably grasped by snare 98 such that spiral flange 509 moves into its extended position during removal. Gastroscope 82 is again removed along with implant 500.

If, instead, bead 530 does not pass proximally through spiral flange 509 under application of force via snare 98, scissors 90 may be used to cut first suture 523 distally of knot 529. Inlet 511, plug 526, and the rest of implant 500 may then be removed separately.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A pyloric valve for inhibiting the flow of chyme through the pyloric region of the gastrointestinal tract, the pyloric valve comprising:
   a blocking portion having a longitudinal axis including a disc-shaped inlet and a helical flange, the disc-shaped inlet having an outer circumference spaced radially outward from the longitudinal axis and a recess disposed in the outer circumference, and the helical flange extending along the longitudinal axis and having an outer edge and at least one recess disposed in the outer edge, the helical flange having a contracted position defining a contracted length and a contracted diameter and an extended position defining an extended length and an extended diameter, wherein the extended length is longer than the contracted length and the extended diameter is smaller than the contracted diameter.

2. The pyloric valve of claim 1, wherein the recesses of the disc-shaped inlet and the helical flange are axially aligned when the helical flange is in the contracted position.

3. The pyloric valve of claim 1, wherein the disc-shaped inlet further includes at least one projection extending radially from the outer circumference.

4. The pyloric valve of claim 1, wherein the blocking portion is a proximal portion, and wherein the pyloric valve further comprises an intermediate portion and a distal portion, the intermediate portion including at least one flexible column and a part-spherical portion, the at least one flexible column being connected to the proximal portion, and the part-spherical portion connecting the at least one flexible column to the distal portion.

5. The pyloric valve of claim 4, wherein the distal portion includes a sleeve.

6. The pyloric valve of claim 5, wherein the sleeve includes a tubular surface having one or more apertures.

7. The pyloric valve of claim 5, wherein the sleeve includes a beveled distal end.

8. The pyloric valve of claim 1, wherein the pyloric valve is constructed of silicon.

9. A kit comprising:
the pyloric valve of claim 1; and
an insertion system including a gastroscope, a fluoroscope, a guidewire, a first tube, a second tube larger in diameter than the first tube, and an over-tube larger in diameter than the second tube.

10. A kit comprising:
the pyloric valve of claim 1; and
a removal system including a gastroscope, a fluoroscope, an over-tube, and at least one of a snare, a grasper, and a pair of scissors.

11. A method of inserting a pyloric valve for inhibiting the flow of chyme through the pyloric region of the gastrointestinal tract, the method comprising the steps of:
providing a pyloric valve having a longitudinal axis including a blocking portion having a disc-shaped inlet and a helical flange, the disc-shaped inlet having an outer circumference and a recess disposed in the outer circumference, and the helical flange extending along a longitudinal axis and having an outer edge and at least one recess disposed in the outer edge, the helical flange having a contracted position defining a contracted length and a contracted diameter and an extended position defining an extended length and an extended diameter, wherein the extended length is longer than the contracted length and the extended diameter is smaller than the contracted diameter;
inserting the pyloric valve through a patient's esophagus and into the patient's stomach while the helical flange is in the extended position;
positioning the pyloric valve within the patient's pyloric sphincter; and
manipulating the helical flange from the extended position to the contracted position such that the longitudinal axis of the blocking portion is substantially parallel to the disc-shaped inlet and extends radially outward from the longitudinal axis.

12. The pyloric valve of claim 11, wherein the step of providing a pyloric valve further includes the blocking portion being a proximal portion, and wherein the pyloric valve further comprises an intermediate portion and a distal portion, the intermediate portion including at least one flexible column, the distal portion including a sleeve;
wherein the step of positioning includes positioning the intermediate portion substantially within the pyloric sphincter of the patient.

13. The method of claim 11, wherein the step of manipulating includes forcing the disc-shaped inlet against the helical flange.

* * * * *